US007470695B2

(12) United States Patent
Guzi et al.

(10) Patent No.: US 7,470,695 B2
(45) Date of Patent: *Dec. 30, 2008

(54) N-HETEROARYL PYRAZOLOPYRIMIDINES AS CYCLIN DEPENDENT KINASE INHIBITORS

(75) Inventors: Timothy J. Guzi, Chatham, NJ (US); Kamil Paruch, Garwood, NJ (US); Michael P. Dwyer, Scotch Plains, NJ (US); Ronald J. Doll, Convent Station, NJ (US); Viyyoor M. Girijavallabhan, Parsippany, NJ (US); Lawrence W. Dillard, Skillman, NJ (US); Vinh D. Tran, Fountain Valle, CA (US); Zhen Min He, Princeton, NJ (US); Ray Anthony James, Bristol, PA (US); Haengsoon Park, Plainsboro, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/395,974

(22) Filed: Mar. 31, 2006

(65) Prior Publication Data

US 2006/0235025 A1    Oct. 19, 2006

Related U.S. Application Data

(62) Division of application No. 10/654,157, filed on Sep. 3, 2003, now Pat. No. 7,078,525.

(60) Provisional application No. 60/408,030, filed on Sep. 4, 2002.

(51) Int. Cl.
*C07D 487/04* (2006.01)
*A61K 31/519* (2006.01)
*A61P 35/04* (2006.01)

(52) U.S. Cl. ............... 514/259.3; 544/281; 514/263.32; 514/252.17; 514/183; 514/81; 514/110; 514/234.2; 514/252.16; 514/151; 514/8; 514/9; 514/27; 514/167; 514/15; 514/221; 514/245; 424/649; 424/94.4

(58) Field of Classification Search ............ 514/259.31; 544/281
See application file for complete search history.

(56) References Cited

U.S. PATENT DOCUMENTS

| 5,571,813 | A | 11/1996 | Ruhter et al. |
| 5,602,136 | A | 2/1997 | Ruhter et al. |
| 5,602,137 | A | 2/1997 | Ruhter et al. |
| 5,688,949 | A | 11/1997 | Inoue et al. |
| 5,707,997 | A | 1/1998 | Shoji et al. |
| 5,919,815 | A | 7/1999 | Bradley et al. |
| 6,040,321 | A | 3/2000 | Kim et al. |
| 6,191,131 | B1 | 2/2001 | He et al. |
| 6,262,096 | B1 | 7/2001 | Kim et al. |
| 6,413,974 | B1 | 7/2002 | Dumont et al. |
| 6,723,136 | B2 | 4/2004 | Pruche |
| 2002/0124330 | A1 | 9/2002 | Pruche |
| 2002/0178512 | A1 | 12/2002 | Pastore et al. |

FOREIGN PATENT DOCUMENTS

| DE | 102 23 917 A1 | 12/2003 |
| EP | 0 628 559 | 4/2002 |
| EP | 1 210 931 B1 | 6/2002 |
| EP | 1 334 973 A | 8/2003 |
| WO | WO 95/35298 | 12/1995 |
| WO | WO 01/62220 A1 | 8/2001 |
| WO | WO 02/40485 | 5/2002 |
| WO | WO 02/50079 | 6/2002 |
| WO | WO 03/091256 | 11/2003 |
| WO | WO 2004/087707 | 10/2004 |

OTHER PUBLICATIONS

Fischer, P.M.; Gianella-Borrador A.;CDK inhibitors in clinical development for the treatment of cancer, Expert. Opin. Investig. Drugs; 2003; 12(6); 955-970.*
Fischer, P.M.; Gianella-Borradori, A.; Recent progress in the discovery and development of cyclin-dependent kinase inhibitors, Expert. Opin. Investig. Drugs; 2005; 14(4); 457-477.*
Vesely et al., "Inhibition of Cyclin-Dependent Kinases by Purine Analogues", Eur. J. Biochem, 224: 771-786 (1994).
Kim et al., "Discovery of Aminothiazole Inhibitors of Cyclin-Dependent Kinase 2: Synthesis, X-ray Crystallographic Analysis, and Biological Activities", *Journal of Medical Chemistry*, p. EST:22.3, A-W, (2002).
Mettey et al., "Aloisines, a New Family of CDK/GSK-3 Inhibitors. SAR Study, Crystal Structure in Complex with CDK2, Enzyme Selectivity, and Cellular Effects", *J. Med. Chem.*, 46(2): 222-236 (2003).
Novinson et al., "Synthesis and Antifungal Properties of Certain 7-Alkylaminopyrazolo[1,5-α]pyrimidines", *J. Med. Chem.*, 20(2): 296-299 (1977).
Senderowicz et al., "Phase I Trial of Continous Infusion Flavopiridol, a Novel Cyclin-Dependent Kinase Inhibitor, in Patients with Refractory Neoplasmns", *Journal of Clinical Oncology*, 16(9): 2986-2999 (Sep. 1998).

(Continued)

Primary Examiner—James O. Wilson
Assistant Examiner—Susanna Moore
(74) Attorney, Agent, or Firm—Palaiyur S. Kalyanaraman; Serena Farquharson-Torres

(57) ABSTRACT

In its many embodiments, the present invention provides a novel class of pyrazolo[1,5-a]pyrimidine compounds as inhibitors of cyclin dependent kinases, methods of preparing such compounds, pharmaceutical compositions containing one or more such compounds, methods of preparing pharmaceutical formulations comprising one or more such compounds, and methods of treatment, prevention, inhibition, or amelioration of one or more diseases associated with the CDKs using such compounds or pharmaceutical compositions.

12 Claims, No Drawings

OTHER PUBLICATIONS

Meijer et al., "Biochemical and Cellular Effects of Roscovitine, a Potent and Selective Inhibitor of the Cyclin-Dependent Kinase CDC2, CDK2 and CDK5", *Eur. J. Biochem*, 243:527-536 (1997).

Bible et al., "Cytotoxic Synergy Between Flavopiridol (NSC 649890, L86-8275) and Various Antineoplastic Agents: The Importance of Sequence of Administration", *Cancer Research*, 57: 3375-3380 (Aug. 15, 1997).

Shiota et al., "Synthesis and Structure-Activity Relationship of a New Series of Potent Angiotensin II Receptor Antagonists: Pyrazolo [1,5-α]pyrimidine Derivatives", *Chem. Pharm. Bull.*, 47(7): 928-938 (1999).

Makisumi, Yasuo "Studies on the Azaindolizine Compounds. XI. Synthesis of 6,7-Disubstituted Pyrazolo[1,5-α]pyrimidines", *Chem. Pharm. Bull* (1962), 10: 620-626.

West, Anthony R., "Solid State Chemistry and its Applications", *Wiley*, New York, 358 and 365 (1988).

Fischer, Peter M. et al., "Recent progress in the discovery and development of cyclin-dependent kinase inhibitors", *Expert Opinion on Investigational Drugs*, 14(4): 457-477 (Apr. 2005).

Fischer, Peter M. et al., "CDK inhibitors in clinical developmental for the treatment of cancer", *Expert Opinion on Investigational Drugs*, 12(6): 955-970 (Jun. 2003).

Gray, Nathanael et al., "ATP-site Directed Inhibitors of Cyclin-dependent Kinases", *Current Med. Chem.* 6(9): 859-875; XP-000856195 (Sep. 1999).

Translation of WO 03/91256, "A Rising Sun Communications Ltd. Translation Product", (1-62), (2003).

Hu, B., "S and G2 Phase Roles for Cdk2 Revealed by Inducible Expression of a Dominant-Negative Mutant in Human Cells", *Mol. Cell. Biol.*, 21:(8) 2755-2766 (2001). Exhibit V, Iddb3 the database on investigational drugs (Jun. 1, 2005 update), Avocidib.

Van Del Heuvel, S., Distinct Roles for Cyclin Dependent Kinases in Cell Cycle Control; Science; 262: 2050-2053 (1991). Exhibit VI, Iddb3 the database on investigational drugs (Jun. 1, 2005 update), Seliciclib.

Byrd, J., "Treatment of Relapsed Chronic Lymphocuic Leukemia by 72-Hour continuous Infusion or 1-Hour Bolus Infusion of Flavopiridol: Results from Cancer and Leukemia Group B Study 19805", *Clinical Cancer Research*, 11:(11) 4176-4181 (2005).

Brown, J. "Chronic Lymphocytic Leukemia: A Niche for Flavopiridol?", *Clinical Cancer Research*, 11:(11) 3971-3973 (2005). Exhibit VII, Iddb3 the database on investigational drugs (Jun. 1, 2005 update), SNS-032.

International Search Report for PCT/US03/27405 dated Sep. 3, 2003 for OC01619K—3 Pages, mailing date Dec. 29, 2003.

Chemical Abstract No. 63:10201 English Translation of JP 40002672, downloaded Sep. 1, 2007.

Chemical Abstract No. 65:108095 English Translation of JP 41014423, downloaded Sep. 1, 2007.

Chemical Abstract No. 66:10957 English Translation of JP 41015583, downloaded Sep. 1, 2007.

Chemical Abstract No. 66:10952 English Translation of JP 41016288, downloaded Sep. 1, 2007.

Chemical Abstract No. 105:226617 English Translation of JP 61057587, downloaded Sep. 1, 2007.

Robins et al., "Purine Analog Inhibitors of Xanthine Oxidase—Structure Activity Relationships and Proposed Binding of the Molybdenum Cofactor", *J. Heterocyclic Chem.*, 22:601-634 (1985).

* cited by examiner

N-HETEROARYL PYRAZOLOPYRIMIDINES AS CYCLIN DEPENDENT KINASE INHIBITORS

This application is a divisional of U.S. application Ser. No. 10/654,157 filed Sep. 3, 2003, now U.S. Pat. No. 7,078,525 and claims the benefit of U.S. Provisional Application, Ser. No. 60/408,030, filed Sep. 4, 2002.

FIELD OF THE INVENTION

The present invention relates to pyrazolo[1,5-a]pyrimidine compounds useful as protein kinase inhibitors, pharmaceutical compositions containing the compounds, and methods of treatment using the compounds and compositions to treat diseases such as, for example, cancer, inflammation, arthritis, viral diseases, neurodegenerative diseases such as Alzheimer's disease, cardiovascular diseases, and fungal diseases. This application claims the benefit of priority from U.S. Provisional Patent Application Ser. No. 60/408,030, filed on Sep. 4, 2002.

BACKGROUND OF THE INVENTION

The cyclin-dependent kinases (CDKs) are serine/threonine protein kinases, which are the driving force behind the cell cycle and cell proliferation. Individual CDK's, such as, CDK1, CDK2, CDK3, CDK4, CDK5, CDK6 and CDK7, CDK8 and the like, perform distinct roles in cell cycle progression and can be classified as either G1, S, or G2M phase enzymes. Uncontrolled proliferation is a hallmark of cancer cells, and misregulation of CDK function occurs with high frequency in many important solid tumors. CDK2 and CDK4 are of particular interest because their activities are frequently misregulated in a wide variety of human cancers. CDK2 activity is required for progression through G1 to the S phase of the cell cycle, and CDK2 is one of the key components of the G1 checkpoint. Checkpoints serve to maintain the proper sequence of cell cycle events and allow the cell to respond to insults or to proliferative signals, while the loss of proper checkpoint control in cancer cells contributes to tumorgenesis. The CDK2 pathway influences tumorgenesis at the level of tumor suppressor function (e.g. p52, RB, and p27) and oncogene activation (cyclin E). Many reports have demonstrated that both the coactivator, cyclin E, and the inhibitor, p27, of CDK2 are either over—or underexpressed, respectively, in breast, colon, nonsmall cell lung, gastric, prostate, bladder, non-Hodgkin's lymphoma, ovarian, and other cancers. Their altered expression has been shown to correlate with increased CDK2 activity levels and poor overall survival. This observation makes CDK2 and its regulatory pathways compelling targets for the development years, a number of adenosine 5'-triphosphate (ATP) competitive small organic molecules as well as peptides have been reported in the literature as CDK inhibitors for the potential treatment of cancers. U.S. Pat. No. 6,413,974, col. 1, line 23—col. 15, line 10 offers a good description of the various CDKs and their relationship to various types of cancer.

CDK inhibitors are known. For example, flavopiridol (Formula I) is a nonselective CDK inhibitor that is currently undergoing human clinical trials, A. M. Sanderowicz et al, *J. Clin. Oncol.* (1998) 16, 2986-2999.

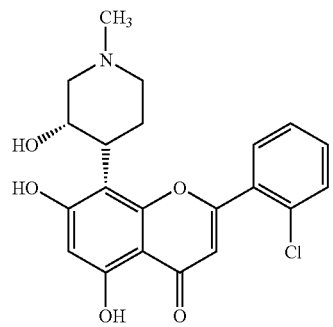

Formula I

Other known inhibitors of the CDKs include, for example, olomoucine (J. Vesely et al, *Eur. J. Biochem.*, (1994) 224, 771-786) and roscovitine (I. Meijer et al, *Eur. J. Biochem.*, (1997) 243, 527-536). U.S. Pat. No. 6,107,305 describes certain pyrazolo[3,4-b] pyridine compounds as CDK inhibitors. An illustrative compound from the '305 patent has the Formula II:

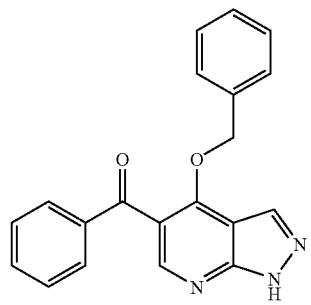

Formula II

K. S. Kim et al, *J. Med. Chem.* 45 (2002) 3905-3927 and WO 02/10162 disclose certain aminothiazole compounds as CDK inhibitors.

Pyrazolopyrimidines are known. For Example, WO92/18504, WO02/50079, WO95/35298, WO02/40485, EP94304104.6, EP0628559 (equivalent to U.S. Pat. Nos. 5,602,136, 5,602,137 and 5,571,813), U.S. Pat. No. 6,383,790, *Chem. Pharm. Bull.*, (1999) 47 928, *J. Med. Chem.*, (1977) 20, 296, *J. Med. Chem.*, (1976) 19 517 and *Chem. Pharm. Bull.*, (1962) 10 620 disclose various pyrazolopyrimidines.

There is a need for new compounds, formulations, treatments and therapies to treat diseases and disorders associated with CDKs. It is, therefore, an object of this invention to provide compounds useful in the treatment or prevention or amelioration of such diseases and disorders.

SUMMARY OF THE INVENTION

In its many embodiments, the present invention provides a novel class of pyrazolo[1,5-a]pyrimidine compounds as inhibitors of cyclin dependent kinases, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the CDKs using such compounds or pharmaceutical compositions.

In one aspect, the present application discloses a compound, or pharmaceutically acceptable salts or solvates of said compound, said compound having the general structure shown in Formula III:

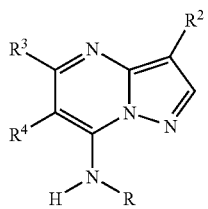

Formula III wherein:

R is heteroaryl, wherein said heteroaryl can be unsubstituted or optionally independently substituted with one or more moieties which can be the same or different, each moiety being independently selected from the group consisting of halogen, alkyl, aryl, cycloalkyl, $CF_3$, $OCF_3$, CN, $-OR^5$, $-NR^5R^6$, $-C(R^4R^5)_nOR^5$, $-C(O_2)R^5$, $-C(O)_2R^5$ $-C(O)NR^5R^6$, $-SR^6$, $-S(O)_2R^7$ $-S(O)_2NR^5R^{6,}-N(R^5)S(O)_2$ $R^7$, $-N(R^5)C(O)R^7$ and $-N(R^5)C(O)NR^5R^6$;

$R^2$ is selected from the group consisting of $R^9$, alkyl, alkynyl, aryl, heteroaryl, $CF_3$, heterocyclylalkyl, alkynylalkyl, cycloalkyl, $-C(O)OR^4$, alkyl substituted with 1-6 $R^9$ groups which can be the same or different and are independently selected from the list of $R^9$ shown later below,

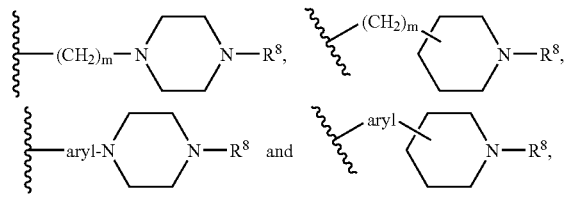

wherein the aryl in the above-noted definitions for $R^2$ can be unsubstituted or optionally substituted with one or more moieties which can be the same or different, each moiety being independently selected from the group consisting of halogen, CN, $-OR^5$, $SR^5$, $-CH_2OR^5$, $-C(O)R^5$, $-SO_3H$, $-S(O)_2R^6$, $-S(O_2)NR^5R^6$, $-NR^5R^6$, $-C(O)NR^5R^6$, $-CF_3$, and $-OCF_3$;

$R^3$ is selected from the group consisting of H, halogen, $-NR^5R^6$, $-C(O)OR^4$, $-C(O)NR^5R^6$, alkyl, alkynyl, cycloalkyl, cycloalkylalkyl, aryl, arylalkyl, heterocyclyl, heterocyclylalkyl, heteroaryl,

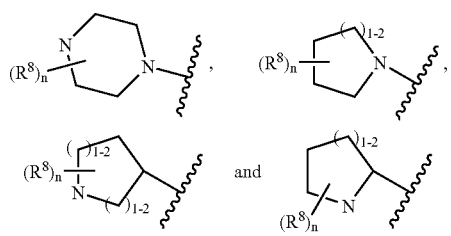

wherein each of said alkyl, cycloalkyl, aryl, arylalkyl, heterocyclyl, heterocyclylalkyl, heteroaryl and heteroarylalkyl for $R^3$ and the heterocyclyl moieties whose structures are shown immediately above for $R^3$ can be substituted or optionally independently substituted with one or more moieties which can be the same or different, each moiety being independently selected from the group consisting of halogen, alkyl, aryl, cycloalkyl, $CF_3$, CN, $-OCF_3$, $-(CR^4R^5)_nOR^5$, $-OR^5$, $-NR^5R^6$, $-(CR^4R^5)_nNR^5R^6$, $-C(O)_2R^5$, $-C(O)R^5$, $-C(O)NR^5R^6$, $-SR^6$, $-S(O)_2R^6$, $-S(O)_2NR^5R^6$, $-N(R^5)S(O)_2R^7$, $-N(R^5)C(O)R^7$ and $-N(R^5)C(O)NR^5R^6$;

$R^4$ is H, halo or alkyl;

$R^5$ is H or alkyl;

$R^6$ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, $CF_3$, $OCF_3$, CN, $-OR^5$, $-NR^5R^{10}$, $-N(R^5)Boc$, $-(CR^4R^5)_nOR^5$, $-C(O)_2R^5$, $-C(O)R^5$, $-C(O)NR^5R^{10}$, $-SO_3H$, $-SR^{10}$, $-S(O)_2R^7$, $-S(O)_2R^5R^{10}$, $-N(R^5)S(O)_2R^7$, $-N(R^5)C(O)R^7$ and $-N(R^5)C(O)NR^5R^{10}$;

$R^{10}$ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, $CF_3$, $OCF_3$, CN, $-OR^5$, $-NR^4R^5$, $-N(R^5)Boc$, $-(CR^4R^5)_nOR^5$, $-C(O)_2R^5$, $-C(O)NR^4R^5$, $-C(O)R^5$, $-SO_3H$, $-SR^5$, $-S(O)_2R^7$, $-S(O)_2R^4R^5$, $-NR^5)S(O)_2)$ $R^7$, $-N(R^5)C(O)R^7$ and $-N(R^5)C(O)NR^4R^5$;

or optionally (i) $R^5$ and $R^{10}$ in the moiety $-NR^5R^{10}$, or (ii) $R^5$ and $R^6$ in the moiety $-NR^5R^6$, may be joined together to form a cycloalkyl or heterocyclyl moiety, with each of said cycloalkyl or heterocyclyl moiety being unsubstituted or optionally independently being substituted with one or more $R^9$ groups;

$R^7$ is selected from the group consisting of alkyl, cycloalkyl, aryl, heteroaryl, arylalkyl and heteroarylalkyl, wherein each of said alkyl, cycloalkyl, heterocyclyl, aryl, heteroaryl and arylalkyl for $R^7$ can be unsubstituted or optionally independently substituted with one or more moieties which can be the same or different, each moiety being independently selected from the group consisting of halogen, alkyl, aryl, cycloalkyl, $CF_3$, $OCF_3$, CN, $-OR^5$, $-NR^5R^{10}$, $-CH_2OR^5$, $-C(O_2)R^5$, $-C(O)NR^5R^{10}$, $-C(O)R^5$, $-SR^{10}$, $-S(O_2)R^{10}$, $-S(O_2)NR^5R^{10}$, $-N(R^5)S(O_2)R^{10}$, $-N(R^5)C(O)R^{10}$ and $-N(R^5)C(O)NR^5R^{10}$;

$R^8$ is selected from the group consisting of $R^6$, $-C(O)NR^5R^{10}$, $-CH_2OR^4$, $-C(O)OR^6$, $-C(O)R^7$ and $-S(O_2)R^7$;

$R^9$ is selected from the group consisting of halogen, $-CN$, $-NR^5R^6$, $-(CH_2)_nOR^4$, $-C(O_2)R^6$, $-C(O)NR^5R^6$, $-OR^6$, $-SR^6$, $-S(O_2)R^7$, $-S(O_2)NR^5R^6$, $-N(R^5)S(O_2)R^7$, $-N(R^5)C(O)R^7$ and $-N(R^5)C(O)NR^5R^6$;

m is 0 to 4; and n is 1 to 4.

The compounds of Formula III can be useful as protein kinase inhibitors and can be useful in the treatment and prevention of proliferative diseases, for example, cancer, inflammation and arthritis. They may also be useful in the treatment of neurodegenerative diseases such Alzheimer's disease, cardiovascular diseases, viral diseases and fungal diseases.

DETAILED DESCRIPTION

In one embodiment, the present invention discloses pyrazolo[1,5-a]pyrimidine compounds which are represented by structural Formula III, or a pharmaceutically acceptable salt or solvate thereof, wherein the various moieties are as described above.

In another embodiment, 2-pyridyl, 4-pyridyl, 3-pyridyl, 4-pyridyl-N-oxide, 3-pyridyl-N-oxide, 1,3-thiazol-2-yl, pyrimidin-5-yl, pyrazin-3-yl and pyridazin-3-yl wherein each of said pyridyl, thiazolyl, pyrimidinyl, pyrazinyl and pyridazinyl moieties can be unsubstituted or optionally independently substituted with one or more moieties which can be the same or different, each moiety being independently selected from the group consisting of halogen, alkyl, arylCF$_3$, OCF$_3$, CN, —OR$^5$, —NR$^5$R$^6$, —CH$_2$OR$^5$, —C(O)$_2$R$^5$, —C(O)NR$^5$R$^6$, —S(O)$_2$)R$^5$R$^6$, and —NR$^5$S(O)$_2$)R$^7$.

In another embodiment, R$^2$ is halogen, CF$_3$, CN, lower alkyl, cycloalkyl, —OR$^6$, —C(O)OR$^4$, —CH$_2$OR$^6$, aryl or heteroaryl.

In another embodiment, R$^3$, is H, halogen, lower alkyl, aryl, heteroaryl, —C(O)OR$^4$, cycloalkyl, —NR$^5$R$^6$, heterocyclylalkyl, cycloalkylalkyl,

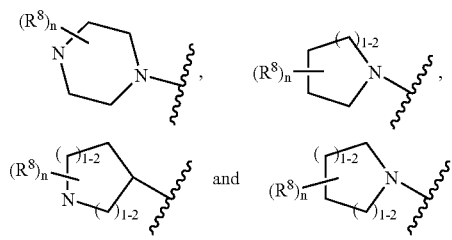

wherein said alkyl, aryl, heteroaryl, heterocyclyl and cycloalkyl for R$^3$ are unsubstituted or optionally independently substituted with one or more moieties which can be the same or different, each moiety being independently selected from the group consisting of halogen, CF$_3$, OCF$_3$, lower alkyl, CN and OR$^5$.

In another embodiment, R$^4$ is H, halo, or lower alkyl.
In another embodiment, R$^5$ is H or lower alkyl.
In another embodiment, m is 0 to 2.
In another embodiment, n is 1 to 2.
In an additional embodiment, R is 2-pyridyl, 4-pyridyl, 3-pyridyl, 4-pyridyl-N-oxide, 3-pyridyl-N-oxide, 1,3-thiazol-2-yl, pyrimidin-5-yl, pyrazin-3-yl and pyridazin-3-yl.
In an additional embodiment, F, Cl, Br, CF$_3$, CN, lower alkyl, cycloalkyl or —(CH$_2$)$_n$OR$^6$.
In an additional embodiment, R$^3$ is H, lower alkyl, cycloalkyl, —C(O)OR$^4$, aryl, heteroaryl, cycloalkylalkyl,

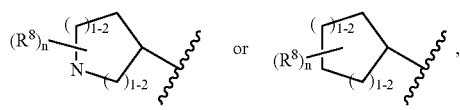

wherein each of said lower alkyl, cycloalkyl, heteroaryl and aryl are unsubstituted or optionally independently substituted with one or more moieties which can be the same or different, each moiety being independently selected from the group consisting of halogen, CF$_3$, lower alkyl, OMe and CN.

In an additional embodiment, R$^3$ is:

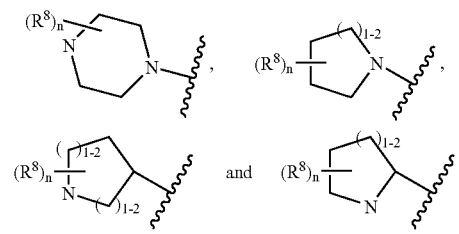

In a still additional embodiment, R$^3$ is

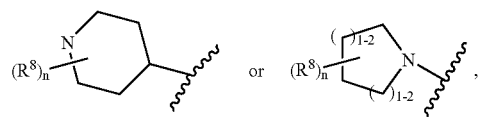

In an additional embodiment, R$^4$ is H.
In an additional embodiment, R$^5$ is H.
In an additional embodiment, m is 0.
In an additional embodiment, n is 1.
An inventive group of compounds are shown in Table 1.

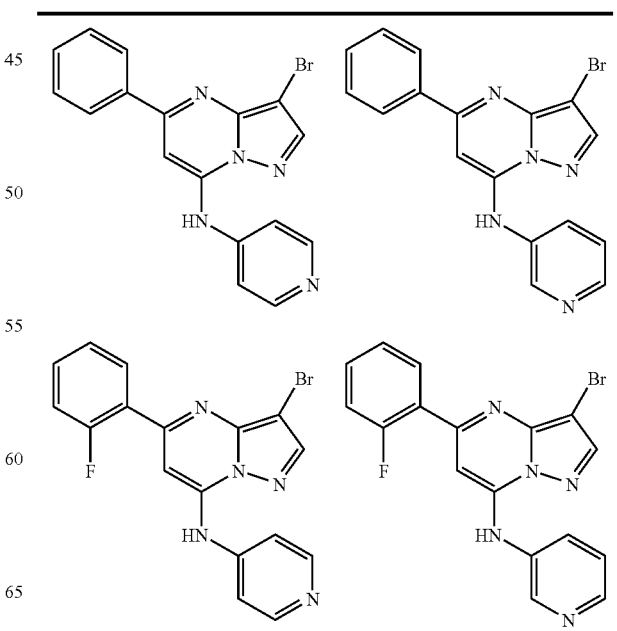

-continued
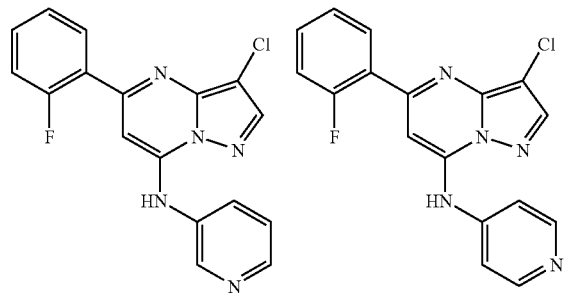
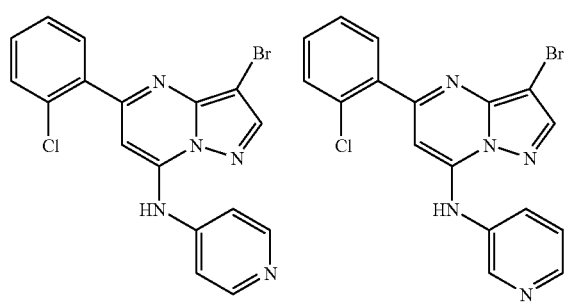
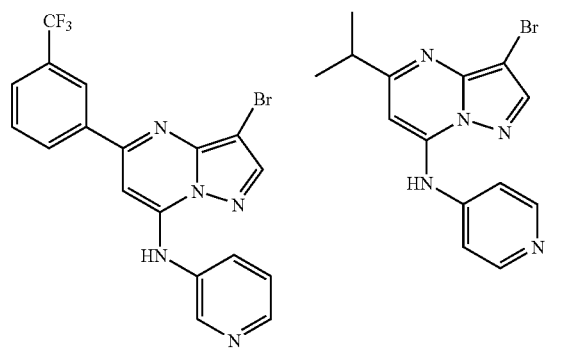
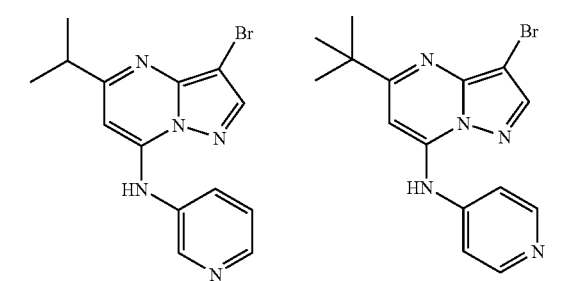
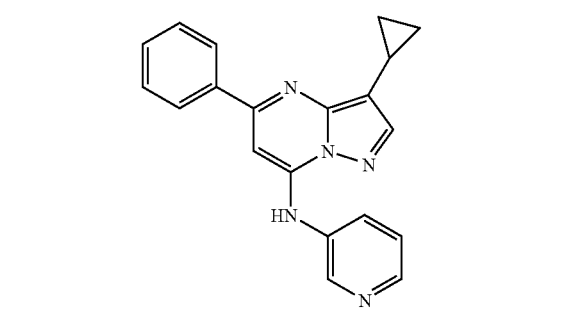
-continued
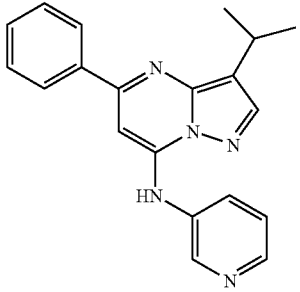
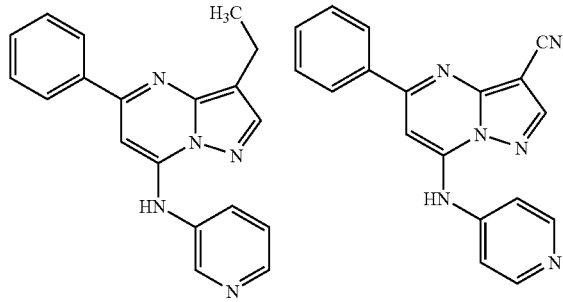
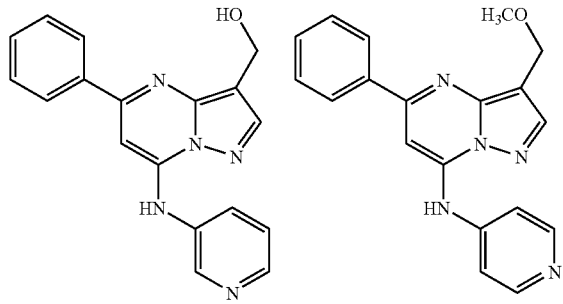
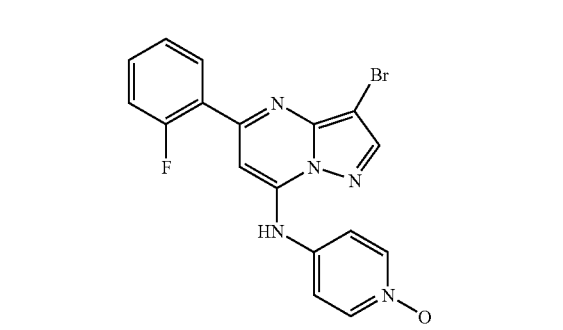
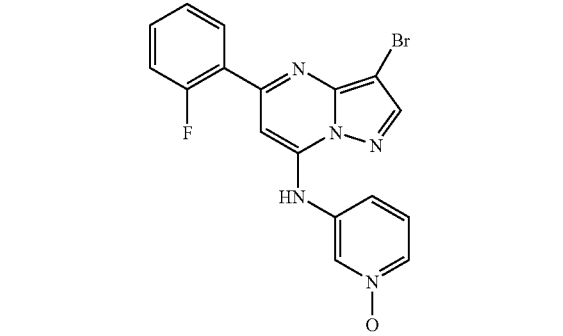

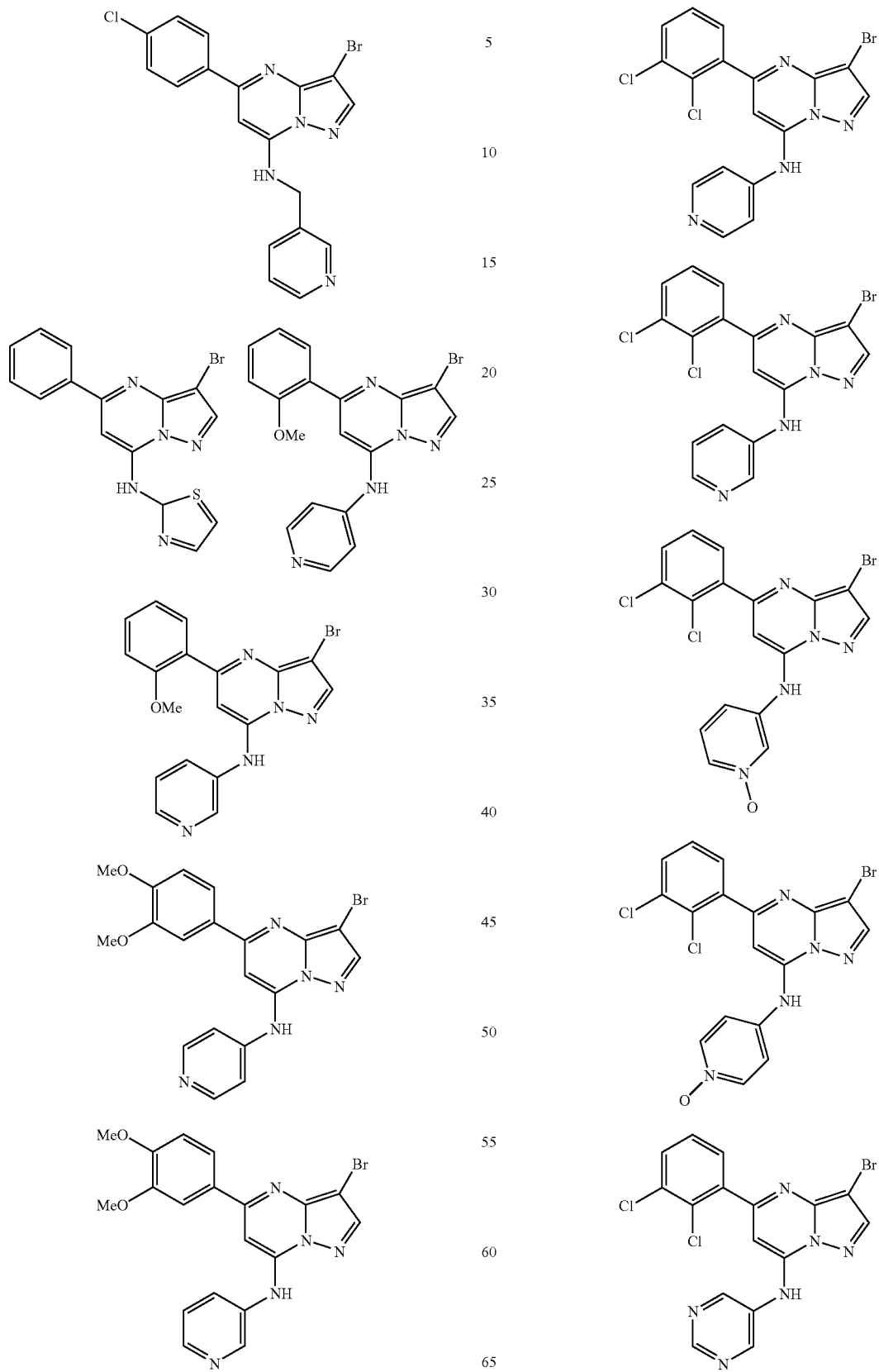

-continued
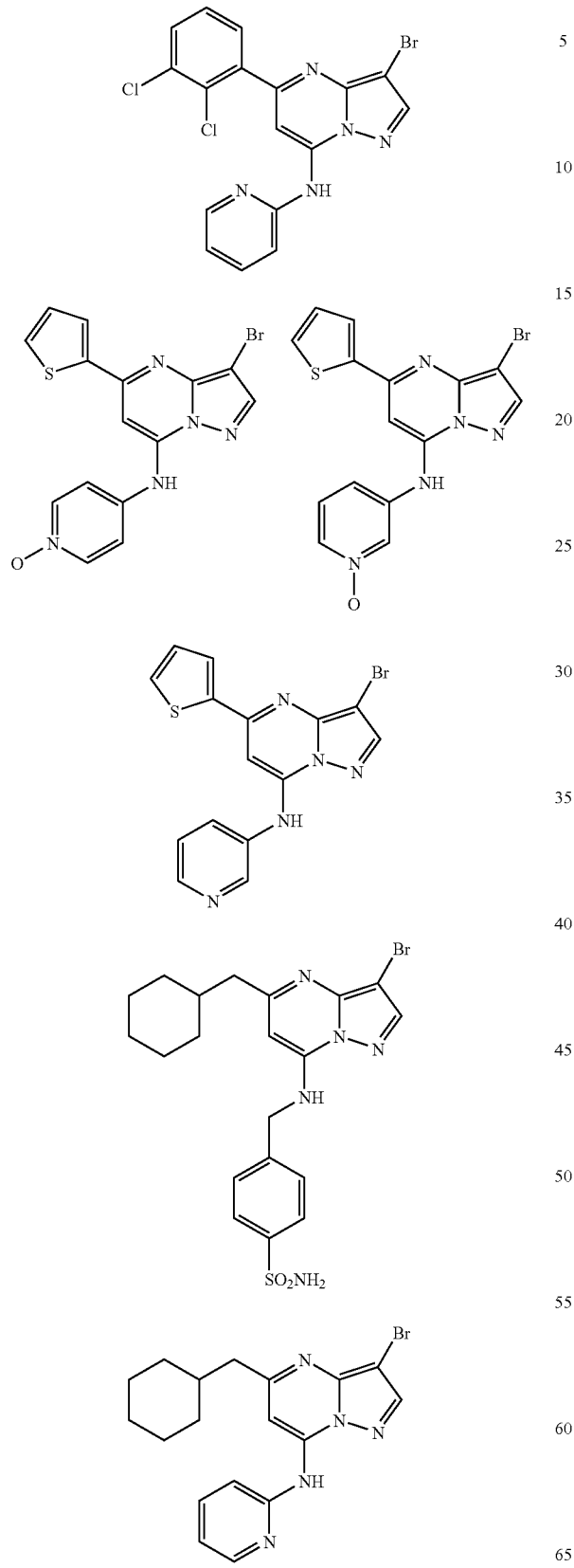
-continued
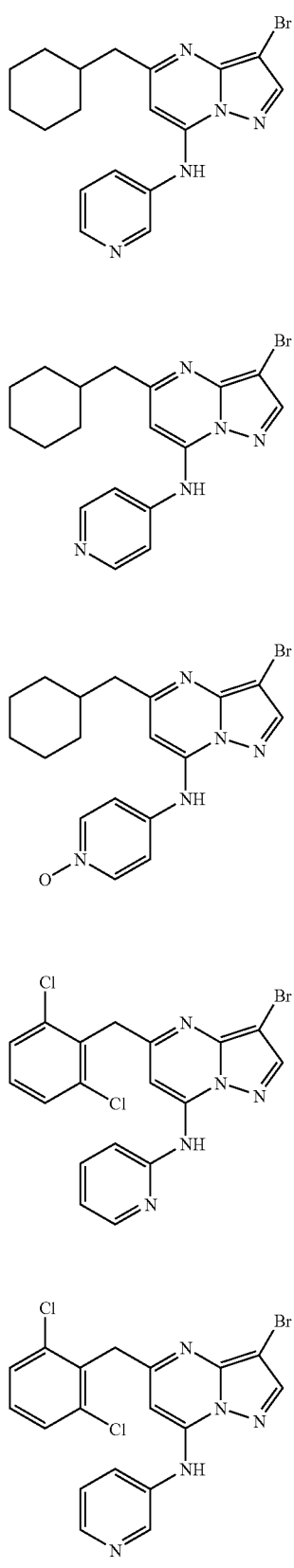

-continued
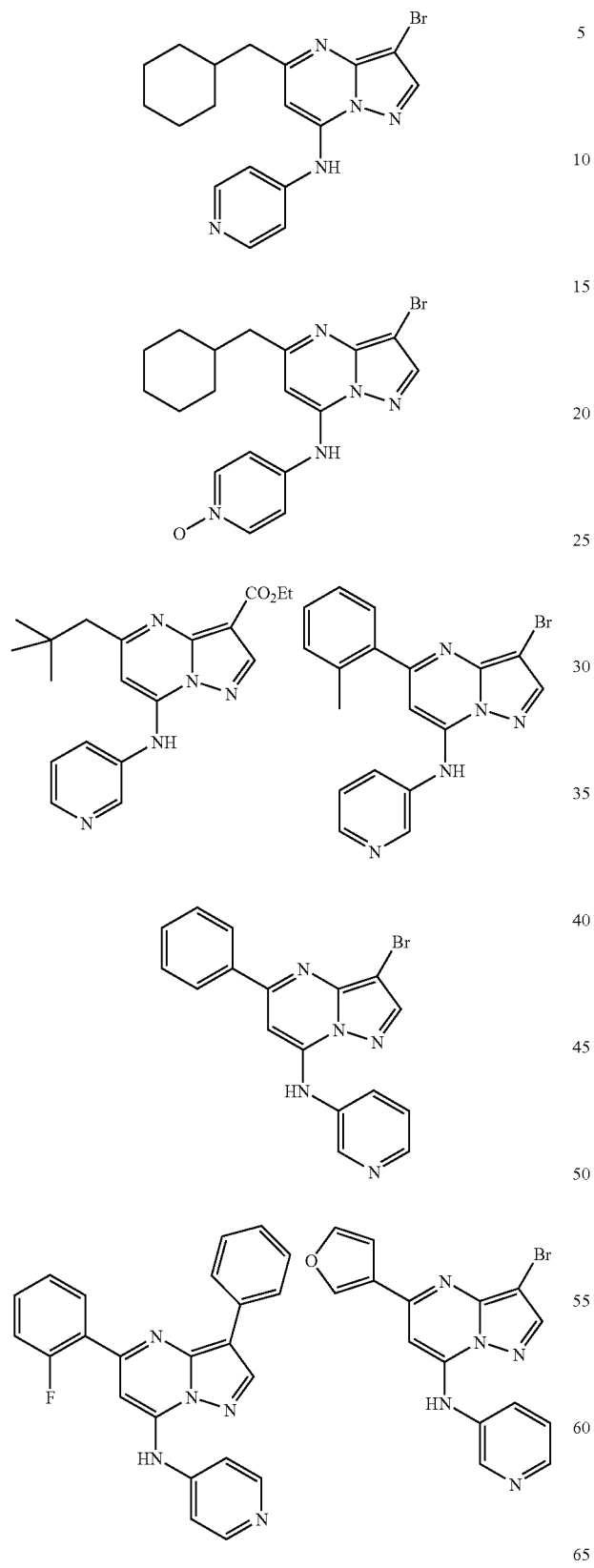
-continued
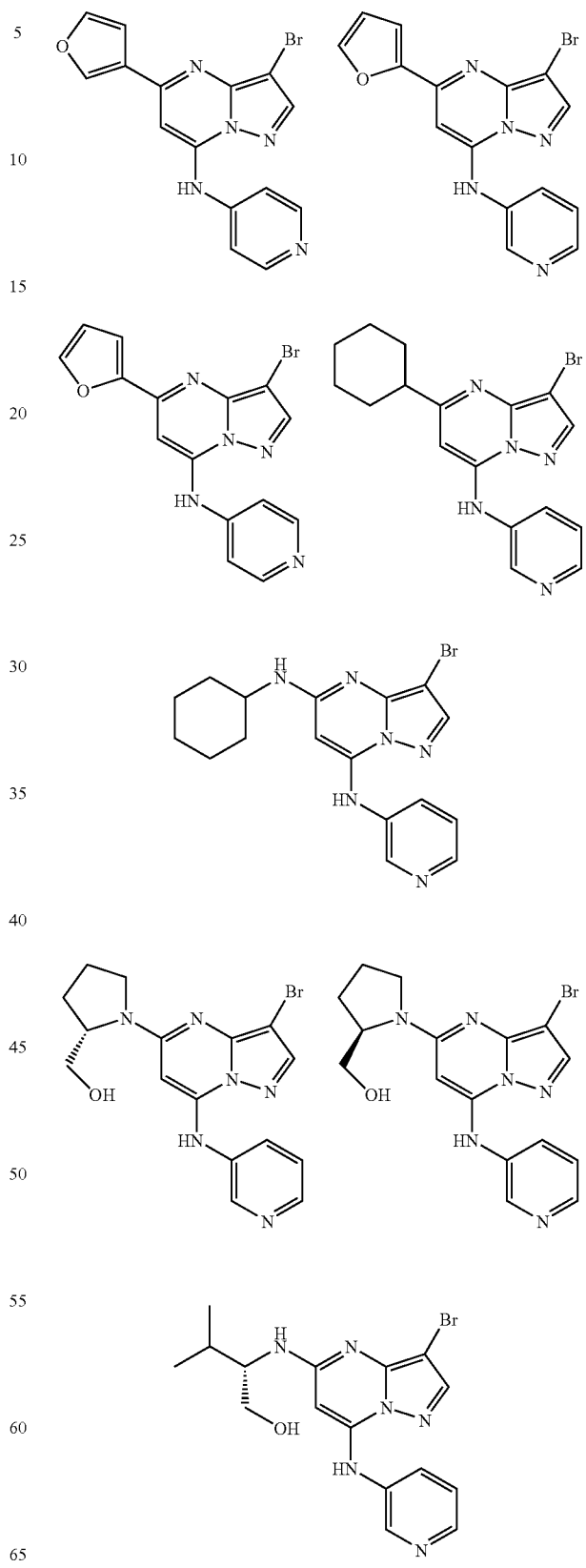

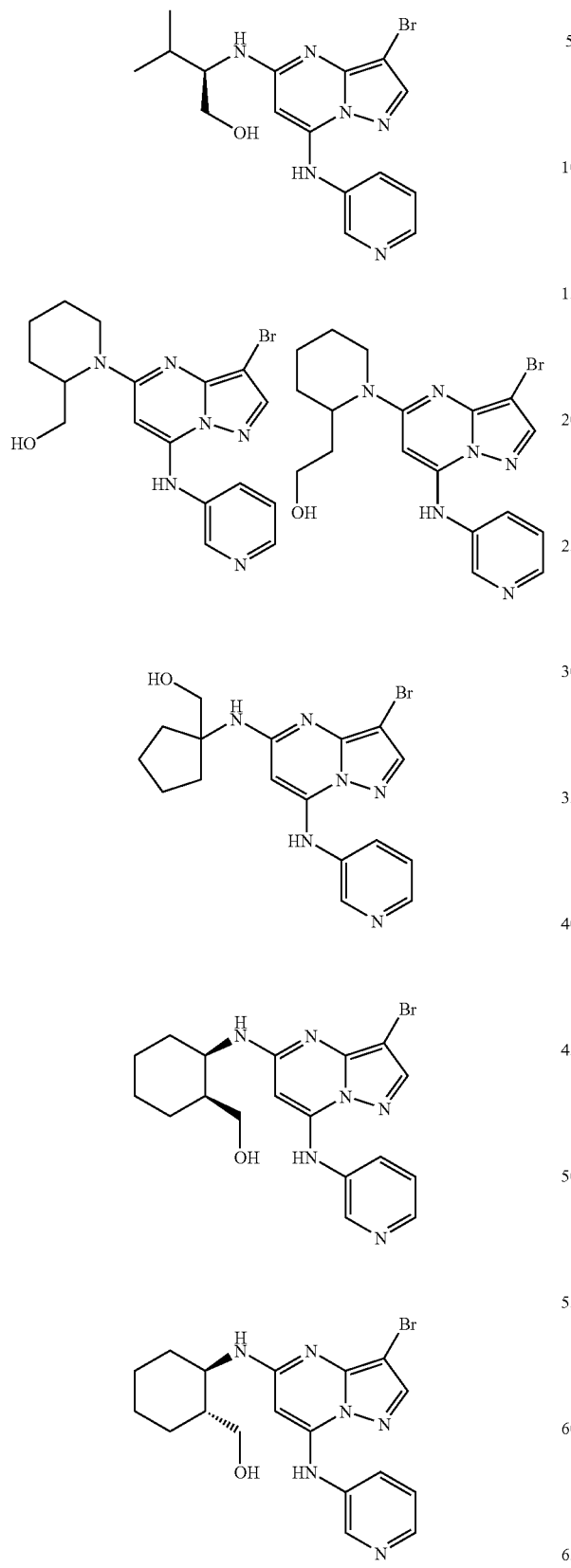
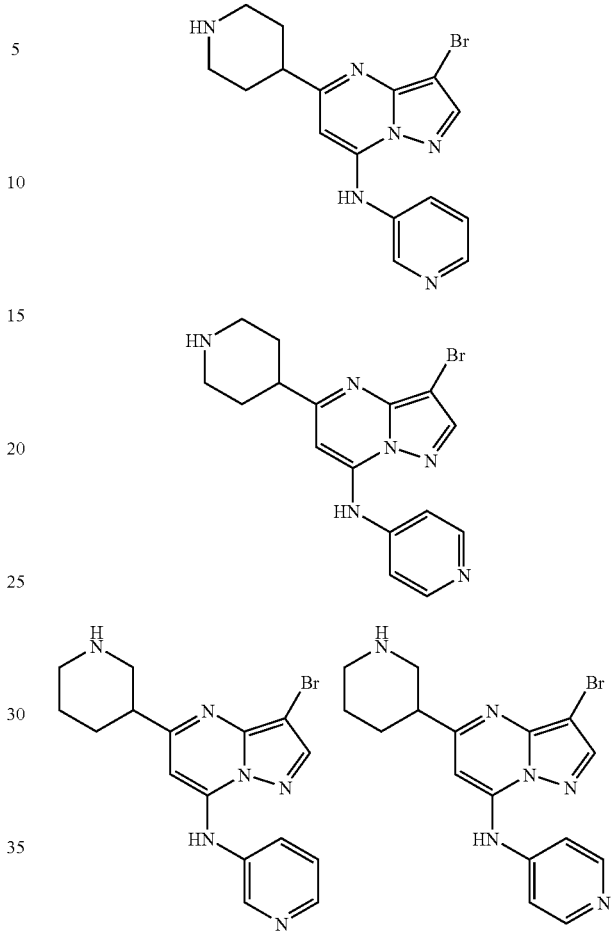

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH (alkyl), —NH(cycloalkyl), —N(alkyl)$_2$, carboxy and —C(O) O-alkyl. Non-limiting examples of suitable alkyl groups include methyl, ethyl, n-propyl, isopropyl and t-butyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryis contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, heteroaralkyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different and are independently selected from the group consisting of hydrogen, alkyl, aryl, and aralkyl.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protected moieties are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

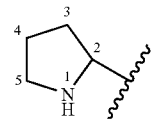

there is no —OH attached directly to carbons marked 2 and 5.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

It should also be noted that any heteroatom with unsatisfied valences in the text, schemes, examples and Tables herein is assumed to have the hydrogen atom to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula III or other Formulas, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula III or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the CDK(s) and thus producing the desired therapeutic, ameliorative, inhibitory or preventative effect.

The compounds of Formula III can form salts which are also within the scope of this invention. Reference to a compound of Formula III herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1)1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N, N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula III, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

The compounds according to the invention have pharmacological properties; in particular, the compounds of Formula III can be inhibitors of protein kinases such as the cyclin dependent kinases (CDKs), for example, CDC2 (CDK1), CDK2, and CDK4, CDK4, CDK5, CDK6, CDK7 and CDK8. The novel compounds of Formula III are expected to be useful in the therapy of proliferative diseases such as cancer, autoimmune diseases, viral diseases, fungal diseases, neurological/neurodegenerative disorders, arthritis, inflammation, antiproliferative (e.g., ocular retinopathy), neuronal, alopecia and cardiovascular disease. Many of these diseases and disorders are listed in U.S. Pat. No. 6,413,974 cited earlier, the disclosure of which is incorporated herein.

More specifically, the compounds of Formula III can be useful in the treatment of a variety of cancers, including (but not limited to) the following: carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of CDKs in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of Formula III may also be useful in the treatment of Alzheimer's disease, as suggested by the recent finding that CDK5 is involved in the phosphorylation of tau protein (*J. Biochem*, (1995) 117, 741-749).

Compounds of Formula III may induce or inhibit apoptosis. The apoptotic response is aberrant in a variety of human diseases. Compounds of Formula III, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of Formula III, as inhibitors of the CDKs, can modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of Formula III may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of Formula III may also be useful in inhibiting tumor angiogenesis and metastasis.

Compounds of Formula III may also act as inhibitors of other protein kinases, e.g., protein kinase C, her2, raf 1, MEK1, MAP kinase, EGF receptor, PDGF receptor, IGF receptor, PI3 kinase, wee1 kinase, Src, Abl and thus be effective in the treatment of diseases associated with other protein kinases.

Another aspect of this invention is a method of treating a mammal (e.g., human) having a disease or condition associated with the CDKs by administering a therapeutically effective amount of at least one compound of Formula III, or a pharmaceutically acceptable salt or solvate of said compound to the mammal.

A preferred dosage is about 0.001 to 500 mg/kg of body weight/day of the compound of Formula III. An especially preferred dosage is about 0.01 to 25 mg/kg of body weight/day of a compound of Formula III, or a pharmaceutically acceptable salt or solvate of said compound.

The compounds of this invention may also be useful in combination (administered together or sequentially) with one or more of anti-cancer treatments such as radiation therapy, and/or one or more anti-cancer agents selected from the group consisting of cytostatic agents, cytotoxic agents (such as for example, but not limited to, DNA interactive agents (such as cisplatin or doxorubicin)); taxanes (e.g. taxotere®, taxol®); topoisomerase II inhibitors (such as etoposide); topoisomerase I inhibitors (such as irinotecan (or CPT-11), camptostar®, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™ (4-[2-[4-[(11R)-3,10-dibromo-8-chloro-6,11-dihydro-5H-benzo[5,6]cyclohepta[1,2-b]pyridin-11-yl-]-1-piperidinyl]-2—oxoehtyl ]-1-piperidinecarboxamide, or SCH 66336 from Schering-Plough Corporation, Kenilworth, N.J.), tipifarnib (Zarnestra® or R115777 from Janssen Pharmaceuticals), L778, 123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as,—Iressa™ (gefitinib) (Astra Zeneca Pharmaceuticals, England), Tarceva™ (erlotinib hydrochloride) (EGFR kinase inhibitors), antibodies to EGFR (e.g., C225), GLEEVEC™ (imatinib) (C-abl kinase inhibitor from Novartis Pharmaceuticals, East Hanover, N.J.); interferons such as, for example, Intron™ A(interferon alpha-2b (recombinant)from Schering-Plough Corporation), Peg-Intron™ (from Schering-Plough Corporation); hormonal therapy combinations; aromatase combinations; ara-C, adriamycin™, cytoxan™, and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine™, 6-Mercaptopurine, 6-Thioguanine, Fludarabine phosphate, oxaliplatin, leucovirin, oxaliplatin (ELOXATIN™ from Sanofi-Synthelabo Pharmaeuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene™ (vinorelbine), Anastrazole, Letrazole, Capecitabine, Reloxafine, Droloxafine, or Hexamethylmelamine.

If formulated as a fixed dose, such combination products employ the compounds of this invention within the dosage range described herein and the other pharmaceutically active agent or treatment within its dosage range. For example, the CDC2 inhibitor olomucine has been found to act synergistically with known cytotoxic agents in inducing apoptosis (*J. Cell Sci.*, (1995) 108, 2897. Compounds of Formula III may also be administered sequentially with known anticancer or cytotoxic agents when a combination formulation is inappropriate. The invention is not limited in the sequence of administration; compounds of Formula III may be administered either prior to or after administration of the known anticancer or cytotoxic agent. For example, the cytotoxic activity of the cyclin-dependent kinase inhibitor flavopiridol is affected by the sequence of administration with anticancer agents. *Cancer Research*, (1997) 57, 3375. Such techniques are within the skills of persons skilled in the art as well as attending physicians.

Accordingly, in an aspect, this invention includes combinations comprising an amount of at least one compound of Formula III, or a pharmaceutically acceptable salt or solvate thereof, and an amount of one or more anti-cancer treatments and anti-cancer agents listed above wherein the amounts of the compounds/treatments result in desired therapeutic effect.

The pharmacological properties of the compounds of this invention may be confirmed by a number of pharmacological assays. The exemplified pharmacological assays which are described later have been carried out with the compounds according to the invention and their salts.

This invention is also directed to pharmaceutical compositions which comprise at least one compound of Formula III, or a pharmaceutically acceptable salt or solvate of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula III, or a pharmaceutically acceptable salt or solvate of said compound and a pharmaceutically acceptable carrier, vehicle or diluent.

Yet another aspect of this invention is a kit comprising an amount of at least one compound of Formula III, or a pharmaceutically acceptable salt or solvate of said compound and an amount of at least one anticancer therapy and/or anticancer agent listed above, wherein the amounts of the two or more ingredients result in desired therapeutic effect.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The retention time and observed parent ion are given.

The following solvents and reagents may be referred to by their abbreviations in parenthesis:

Thin layer chromatography: TLC dichloromethane: CH$_2$Cl$_2$ ethyl acetate: AcOEt or EtOAc methanol: MeOH trifluoroacetate: TFA triethylamine: Et$_3$N or TEA butoxycarbonyl: n-Boc or Boc nuclear magnetic resonance spectroscopy: NMR liquid chromatography mass spectrometry: LCMS high resolution mass spectrometry: HRMS milliliters: mL millimoles: mmol microliters: µl grams: g milligrams: mg room temperature or rt (ambient): about 25° C.

EXAMPLES

In general, the compounds of the present invention can be prepared through the general routes described below in Scheme 1. Treatment of the Scheme 1

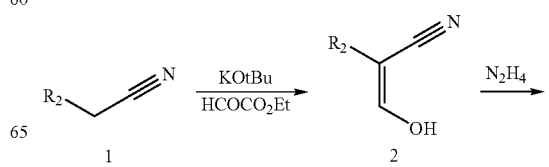

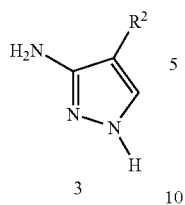

starting nitrile with potassium t-butoxide and ethyl formate gives rise to the intermediate enol 2 which upon treatment with hydrazine gives the desired substituted 3-aminopyrazole. Condensation of the compounds of type 3 with the appropriately functionalized keto ester of type 5 gives rise to the pyridones 6 as shown in Scheme 3. The keto esters used in this general route are either commercially available or can be made as illustrated in Scheme 2.

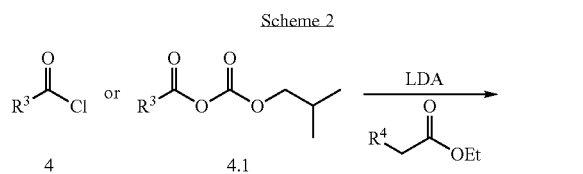

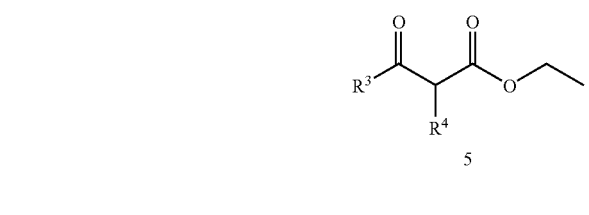

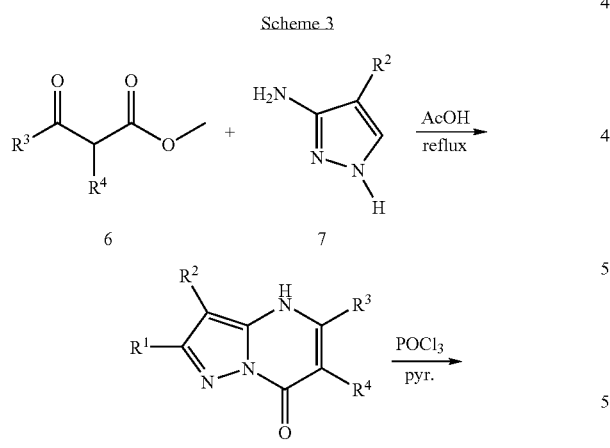

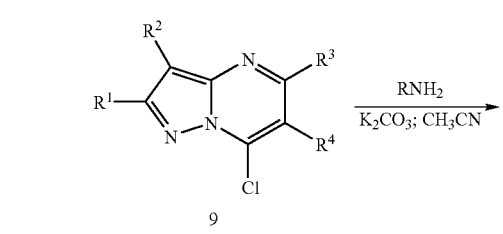

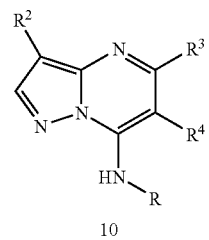

The chlorides of type 9 can be prepared by treatment of the pyridones 8 with $POCl_3$. When $R^2$ is equal to H, substitution in this position is possible on the compounds of type 9 by electrophilic halogenation, acylation, and various other electrophilic aromatic substitutions.

Introduction of the N7-amino functionality can be accomplished through displacement of the chloride of compounds of type 9 by reaction with the appropriate amine as shown in Scheme 3.

When $R^3$=OEt in compounds of type 6, the dichlorides of type 12 can easily be prepared as outlined in Scheme 4. Selective displacements of the 7-chloride gives rise to compounds of type 13, which can readily be converted to products of type 14.

SCHEME 4

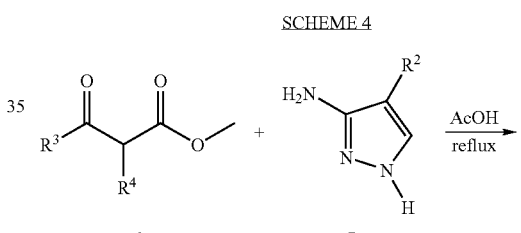

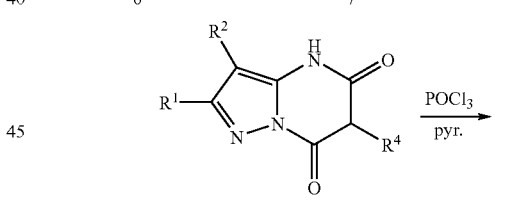

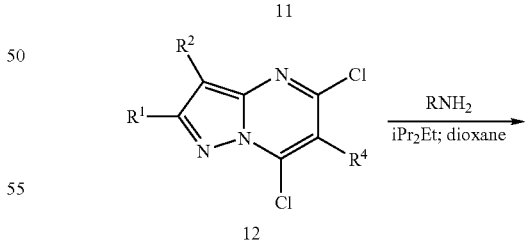

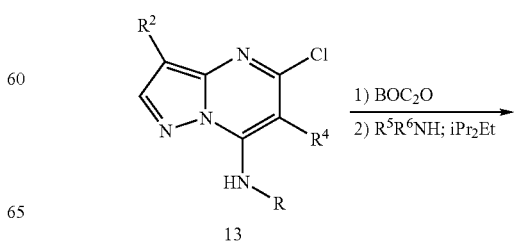

-continued

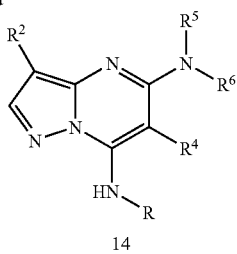

14

Preparative Examples

Preparative Example 1

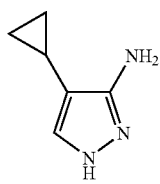

Step A:

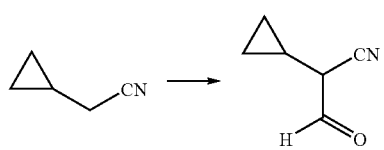

A procedure in German patent DE 19834047 A1, p 19 was followed. To a solution of KOtBu (6.17 g, 0.055 mol) in anhydrous THF (40 mL) was added, dropwise, a solution of cyclopropylacetonitrile (2.0 g, 0.025 mol) and ethyl formate (4.07 g, 0.055 mol) in anhydrous THF (4 mL). A precipitate formed immediately. This mixture was stirred for 12 hr. It was concentrated under vacuum and the residue stirred with $Et_2O$ (50 mL). The resulting residue was decanted and washed with $Et_2O$ (2×50 mL) and $Et_2O$ removed from the residue under vacuum. The residue was dissolved in cold $H_2O$ (20 mL) and pH adjusted to 4-5 with 12 N HCl. The mixture was extracted with $CH_2Cl_2$ (2×50 mL). The organic layers were combined, dried over $MgSO_4$ and concentrated under vacuum to give the aldehyde as a tan liquid.

Step B:

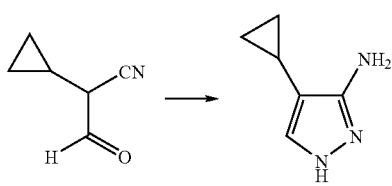

The product from Preparative Example 1, Step A (2.12 g, 0.0195 mol), $NH_2NH_2H_2O$ (1.95 g, 0.039 mol) and 1.8 g (0.029 mole) of glacial $CH_3CO_2H$ (1.8 g, 0.029 mol) were dissolved in EtOH (10 mL). It was refluxed for 6 hr and concentrated under vacuum. The residue was slurried in $CH_2Cl_2$ (150 mL) and the pH adjusted to 9 with 1N NaOH. The organic layer was washed with brine, dried over $MgSO_4$ and concentrated under vacuum to give the product as a waxy orange solid.

Preparative Examples 2-4

By essentially the same procedure set forth in Preparative Example 1, only substituting the nitrile shown in Column 2 of Table 2, the compounds in Column 3 of Table 2 were prepared:

TABLE 2

| Prep. Ex. | Column 2 | Column 3 |
|---|---|---|
| 2 | | |
| 3 | $H_3C$—CN | $H_3C$—pyrazole-$NH_2$ |

Preparative Example 4

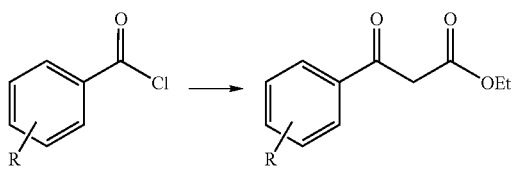

The reactions were done as outlined in (K. O. Olsen, *J. Org. Chem.*, (1987) 52, 4531-4536). Thus, to a stirred solution of lithium diisopropylamide in THF at −65 to −70° C. was added freshly distilled ethyl acetate, dropwise. The resulting solution was stirred for 30 min and the acid chloride was added as a solution in THF. The reaction mixture was stirred at −65 to −70° C. for 30 min and then terminated by the addition of 1 N HCl solution. The resulting two-phased mixture was allowed to warm to ambient temperature. The resulting mixture was diluted with EtOAc (100 mL) the organic layer was collected. The aqueous layer was extracted with EtOAc (100 mL). The organic layers were combined, washed with brine, dried ($Na_2SO_4$), and concentrated in vacuo to give the crude β-keto esters, which were used in the subsequent condensations.

Preparative Examples 5-10

By essentially the same procedure set forth in Preparative Example 4 only ting the acid chlorides shown in Column 2 of Table 3, the β-keto esters in Column 3 of Table 3 were prepared:

TABLE 3

| Prep. Ex. | Column 2 | Column 3 | DATA |
|---|---|---|---|
| 5 | 2-methoxybenzoyl chloride | ethyl 3-(2-methoxyphenyl)-3-oxopropanoate | Yield = 99%<br>LCMS: MH$^+$ = 223 |
| 6 | 3,4-dimethoxybenzoyl chloride | ethyl 3-(3,4-dimethoxyphenyl)-3-oxopropanoate | Yield = 99%<br>LCMS: MH$^+$ = 253 |
| 7 | 2,3-dichlorobenzoyl chloride | ethyl 3-(2,3-dichlorophenyl)-3-oxopropanoate | Yield = 80%<br>LCMS: MH$^+$ = 261 |
| 8 | thiophene-2-carbonyl chloride | ethyl 3-oxo-3-(thiophen-2-yl)propanoate | Yield = 93%<br>MH$^+$ = 199 |
| 9 | 3,3-dimethylbutanoyl chloride | ethyl 5,5-dimethyl-3-oxohexanoate | Yield = 93% |
| 10 | 2-methylbenzoyl chloride | ethyl 3-(2-methylphenyl)-3-oxopropanoate | Yield = 100% |

Preparative Example 11

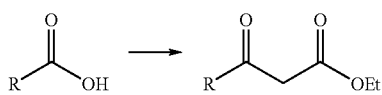

To a solution of the acid in THF was added Et$_3$N, followed by isobutyl chloroformate at –20 to –30° C. After the mixture was stirred for 30 min at –20 to –30° C., triethylamine hydrochloride was filtered off under argon, and the filtrate was added to the LDA-EtOAc reaction mixture (prepared as outlined in Method A) at –65 to –70° C. After addition of 1 N HCl, followed by routine workup of the reaction mixture and evaporation of the solvents, the crude β-keto esters were isolated. The crude material was used in the subsequent condensations.

Preparative Examples 12 and 13

By essentially the same conditions set forth in Preparative Example 11 only substituting the carboxylic acid shown in Column 2 of Table 4, the compounds shown in Column 3 of Table 4 were prepared:

TABLE 4

| Prep. Ex. | Column 2 | Column 3 | DATA |
|---|---|---|---|
| 12 | cyclohexyl-CH₂-COOH | cyclohexyl-CH₂-C(O)-CH₂-C(O)-OEt | Yield = 99%<br>$MH^+$ = 213 |
| 13 | 2,6-dichlorophenyl-CH₂-COOH | 2,6-dichlorophenyl-CH₂-C(O)-CH₂-C(O)-OEt | Yield = 70%<br>$MH^+$ = 275 |
| 13.10 | cyclohexyl-C(O)-Cl | cyclohexyl-C(O)-CH₂-C(O)-OEt | Yield = 99<br>$MH^+$ = 199 |
| 13.11 | CbzN-piperidin-4-yl-C(O)-Cl | CbzN-piperidin-4-yl-C(O)-CH₂-C(O)-OEt | Yield = 99<br>$MH^+$ = 334 |
| 13.12 | CbzN-piperidin-3-yl-C(O)-Cl | CbzN-piperidin-3-yl-C(O)-CH₂-C(O)-OEt | Yield = 99<br>$MH^+$ = 334 |

Preparative Example 14

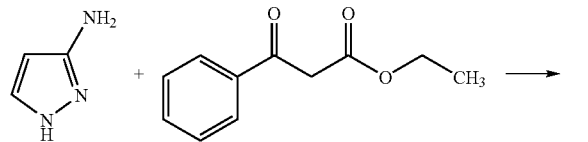

A solution of 3-aminopyrazole (2.0g, 24.07 mmol) and ethyl benzoylacetate (4.58 mL, 1.1 eq.) in AcOH (15 mL) was heated at reflux for 3 hours. The reaction mixture was cooled to room temperature and concentrated in vacuo. The resulting solid was diluted with EtOAc and filtered to give a white solid (2.04 g, 40% yield).

Preparative Examples 15-32.15

By essentially the same procedure set forth in Preparative Example 14 only substituting the aminopyrazole shown in Column 2 of Table 5 and the ester shown in Column 3 of Table 5, the compounds shown in Column 4 of Table 5 were prepared:

TABLE 5

| Prep. Ex. | Column 2 | Column 3 | Column 4 |
|---|---|---|---|
| 15 | 3-aminopyrazole | ethyl (2-fluorobenzoyl)acetate | 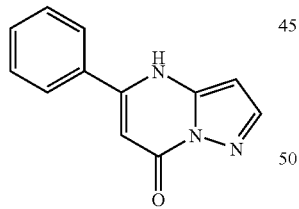 |

TABLE 5-continued

| Prep. Ex. | Column 2 | Column 3 | Column 4 |
|---|---|---|---|
| 16 | 3-amino-1H-pyrazole | ethyl 3-(2-chlorophenyl)-3-oxopropanoate | 5-(2-chlorophenyl)-4H-pyrazolo[1,5-a]pyrimidin-7-one |
| 17 | 3-amino-1H-pyrazole | ethyl 3-oxo-3-(3-(trifluoromethyl)phenyl)propanoate | 5-(3-(trifluoromethyl)phenyl)-4H-pyrazolo[1,5-a]pyrimidin-7-one |
| 18 | 3-amino-1H-pyrazole | ethyl 4-methyl-3-oxopentanoate | 5-isopropyl-4H-pyrazolo[1,5-a]pyrimidin-7-one |
| 19 | 3-amino-1H-pyrazole | ethyl 4,4-dimethyl-3-oxopentanoate | 5-tert-butyl-4H-pyrazolo[1,5-a]pyrimidin-7-one |
| 20 | 3-amino-4-cyclopropyl-1H-pyrazole | ethyl 3-oxo-3-phenylpropanoate | 3-cyclopropyl-5-phenyl-4H-pyrazolo[1,5-a]pyrimidin-7-one |
| 21 | 3-amino-4-isopropyl-1H-pyrazole | ethyl 3-oxo-3-phenylpropanoate | 3-isopropyl-5-phenyl-4H-pyrazolo[1,5-a]pyrimidin-7-one |
| 22 | 3-amino-4-ethyl-1H-pyrazole | ethyl 3-oxo-3-phenylpropanoate | 3-ethyl-5-phenyl-4H-pyrazolo[1,5-a]pyrimidin-7-one |

TABLE 5-continued

| Prep. Ex. | Column 2 | Column 3 | Column 4 |
| --- | --- | --- | --- |
| 23 | | | |
| 24 | | | |
| 25 | | | |
| 26 | | | |
| 27 | | | |
| 28 | | | |
| 29 | | | |

TABLE 5-continued

| Prep. Ex. | Column 2 | Column 3 | Column 4 |
|---|---|---|---|
| 30 | 3-aminopyrazole | ethyl 5,5-dimethyl-3-oxohexanoate | 5-neopentyl-4H-pyrazolo[1,5-a]pyrimidin-7-one |
| 31 | ethyl 3-amino-1H-pyrazole-4-carboxylate | ethyl 5,5-dimethyl-3-oxohexanoate | ethyl 5-neopentyl-7-oxo-4,7-dihydropyrazolo[1,5-a]pyrimidine-3-carboxylate |
| 32 | 3-aminopyrazole | ethyl 3-(2-methylphenyl)-3-oxopropanoate | 5-(2-methylphenyl)-4H-pyrazolo[1,5-a]pyrimidin-7-one |
| 32.11 | 3-aminopyrazole | ethyl 3-(furan-3-yl)-3-oxopropanoate | 5-(furan-3-yl)-4H-pyrazolo[1,5-a]pyrimidin-7-one |
| 32.12 | 3-aminopyrazole | ethyl 3-(furan-2-yl)-3-oxopropanoate | 5-(furan-2-yl)-4H-pyrazolo[1,5-a]pyrimidin-7-one |
| 32.13 | 3-aminopyrazole | ethyl 3-(1-Cbz-piperidin-4-yl)-3-oxopropanoate | 5-(1-Cbz-piperidin-4-yl)pyrazolo[1,5-a]pyrimidin-7-ol |
| 32.14 | 3-aminopyrazole | ethyl 3-(1-Cbz-piperidin-3-yl)-3-oxopropanoate | 5-(1-Cbz-piperidin-3-yl)pyrazolo[1,5-a]pyrimidin-7-ol |

TABLE 5-continued

| Prep. Ex. | Column 2 | Column 3 | Column 4 |
|---|---|---|---|
| 32.15 | | | |

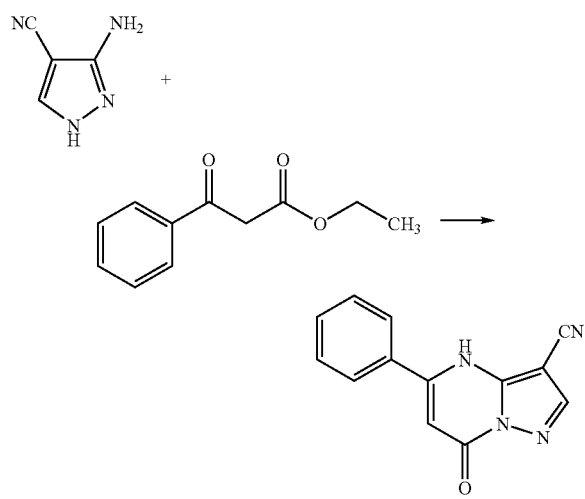

Preparative Example 33

Ethyl benzoylacetate (1.76 mL, 1.1 eq.) and 3-amino-4-cyanopyrazole (1.0 g, 9.25 mmol) in ACOH (5.0 mL) and H$_2$O (10 mL) was heated at reflux 72 hours. The resulting solution was cooled to room temperature, concentrated in vacuo, and diluted with EtOAc. The resulting precipitate was filtered, washed with EtOAc, and dried in vacuo (0.47 g, 21% yield).

Preparative Example 33.10

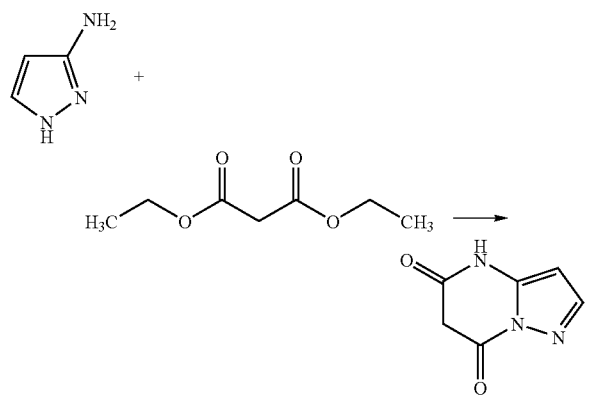

A procedure in U.S. Pat. No. 3,907,799 was followed. Sodium (2.3 g, 2 eq.) was added to EtOH (150 mL) portionwise. When the sodium was completely dissolved, 3-aminopyrazole (4.2 g, 0.05 mol) and diethyl malonate (8.7 g, 1.1 eq.) were added and the resulting solution heated to reflux for 3 hours. The resulting suspension was cooled to room temperature and filtered. The filter cake was washed with EtOH (100 mL) and dissolved in water (250 mL). The resulting solution was cooled in an ice bath and the pH adjusted to 1-2 with concentrated HCl. The resulting suspension was filtered, washed with water (100 mL) and dried under vacuum to give a white solid (4.75 g, 63% yield).

Preparative Examples 33.11-33.12

By essentially the same procedure set forth in Preparative Example 33.10 only substituting the compound shown in Column 2 of Table 5.1, the compounds shown in Column 3 of Table 5.1 are prepared:

TABLE 5.1

| Prep. Ex. | Column 2 | Column 3 |
|---|---|---|
| 33.11 | | |
| 33.12 | | |

Preparative Example 34

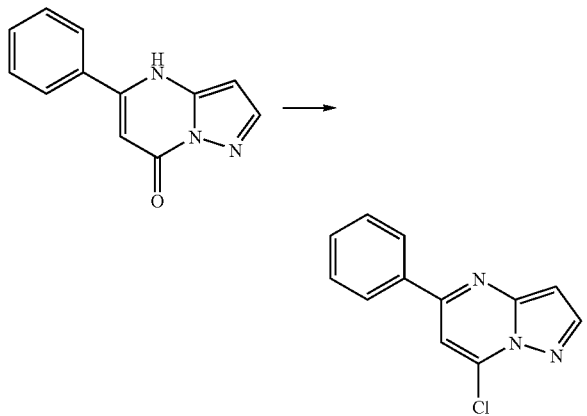

A solution of the compound prepared in Preparative Example 14 (1.0 g, 4.73 mmol) in POCl$_3$ (5 mL) and pyridine (0.25 mL) was stirred at room temperature 3 days. The resulting slurry was diluted with Et$_2$O, filtered, and the solid residue washed with Et$_2$O. The combined Et$_2$O washings were cooled to 0° C. and treated with ice. When the vigorous reaction ceased, the resulting mixture was diluted with H$_2$O, separated, and the aqueous layer extracted with Et$_2$O. The combined organics were washed with H$_2$O and saturated NaCl, dried over Na$_2$SO$_4$, filtered, and concentrated to give a pale yellow solid (0.86 g, 79% yield). LCMS: MH$^+$=230.

Preparative Examples 35-53.15

By essentially the same procedure set forth in Preparative Example 34, only substituting the compound shown in Column 2 of Table 6, the compounds shown in Column 3 of Table 6 were prepared:

TABLE 6

| Prep. Ex. | Column 2 | Column 3 | DATA |
|---|---|---|---|
| 35 | | | LCMS: MH$^+$ = 248 |
| 36 | | | |
| 37 | | | LCMS: MH$^+$ = 298 |
| 38 | | | LCMS: MH$^+$ = 196 |

TABLE 6-continued

| Prep. Ex. | Column 2 | Column 3 | DATA |
|---|---|---|---|
| 39 | | | LCMS: MH$^+$ = 210 |
| 40 | | | |
| 41 | | | LCMS: MH$^+$ = 272 |
| 42 | | | |
| 43 | | | LCMS: MH$^+$ = 255 |
| 44 | | | |
| 45 | | | Yield = 65%<br>LCMS: MH$^+$ = 260 |

TABLE 6-continued

| Prep. Ex. | Column 2 | Column 3 | DATA |
|---|---|---|---|
| 46 | | | Yield = 35%<br>LCMS: MH+ = 290 |
| 47 | | | Yield = 32%<br>LCMS: MH+ = 298 |
| 48 | | | Yield = 45%<br>LCMS: MH+ = 236 |
| 49 | | | Yield = 100%<br>LCMS: MH+ = 250 |
| 50 | | | Yield = 88%<br>LCMS: MH+ = 314 |
| 51 | | | Yield = 43%<br>LCMS: MH+ = 223 |
| 52 | | | Yield = 30%<br>LCMS: MH+ = 295 |

TABLE 6-continued

| Prep. Ex. | Column 2 | Column 3 | DATA |
|---|---|---|---|
| 53 | | | Yield = 98%<br>LCMS: MH⁺ = 244 |
| 53.11 | | | |
| 53.12 | | | |
| 53.13 | | | Yield = 96<br>MH⁺ = 371 |
| 53.14 | | | Yield = 99<br>MH⁺ = 371 |
| 53.15 | | | Yield = quant.<br>MH⁺ = 236 |

Preparative Example 53.16

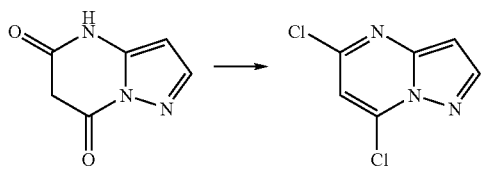

POCl$_3$ (62 mL) was cooled to 5 °C. under nitrogen and dimethylaniline (11.4 g, 2.8 eq.) and the compound prepared in Preparative Example 33.10 (4.75 g, 0.032 mol). The reaction mixture was warmed to 60° C. and stirred overnight. The reaction mixture was cooled to 30° C. and the POCl$_3$ was distilled off under reduced pressure. The residue was dissolved in CH$_2$Cl$_2$ (300 mL) and poured onto ice. After stirring 15 minutes, the pH of the mixture was adjusted to 7-8 with solid NaHCO$_3$. The layers were separated and the organic layer was washed with H$_2$O (3×200 mL), dried over MgSO$_4$, filtered, and concentrated. The crude product was purified by flash chromatography using a 50:50 CH$_2$Cl$_2$:hexanes solution as eluent to elute the dimethyl aniline. The eluent was then changed to 75:25 CH$_2$Cl$_2$:hexanes to elute the desired product (4.58 g, 77% yield). MS: MH$^+$=188.

Preparative Examples 53.17-53.18

By essentially the same procedure set forth in Preparative Example 53.16 only substituting the compound in Column 2 of Table 6.10, the compounds shown in Column 3 of Table 6.10 are prepared:

TABLE 6.10

| Prep. Ex. | Column 2 | Column 3 |
|---|---|---|
| 53.17 | 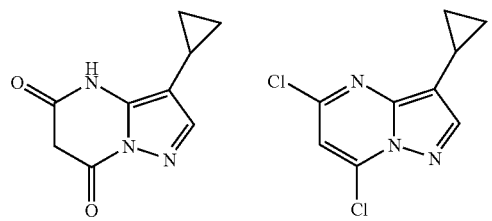 | |
| 53.18 | (structure with CH$_3$, NH, O) | (structure with Cl, CH$_3$) |

Preparative Example 54

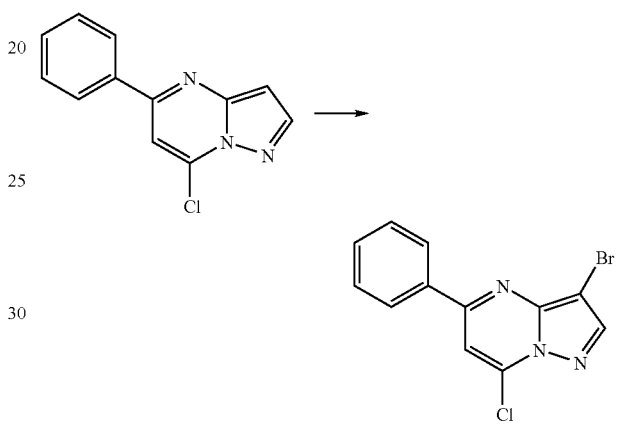

A solution of the compound prepared in Preparative Example 34 (0.10 g, 0.435 mmol) in CH$_3$CN (3 mL) was treated with N-bromosuccinimide ("NBS") (0.085 g, 1.1 eq.). The reaction mixture was stirred at room temperature 1 hour and concentrated under reduced pressure. The crude product was purified by flash chromatography using a 20% EtOAc-in-hexanes solution as eluent (0.13 g, 100% yield). LCMS: MH$^+$=308.

Preparative Examples 55-68.15

By essentially the same procedure set forth in Preparative Example 54 only substituting the compounds shown in Column 2 of Table 7, the compounds shown in Column 3 of Table 7 were prepared:

TABLE 7

| Prep. Ex. | Column 2 | Column 3 | DATA |
|---|---|---|---|
| 55 | (2-F-phenyl pyrazolopyrimidine-Cl) | (2-F-phenyl pyrazolopyrimidine-Cl, Br) | LCMS: MH$^+$ = 326 |

TABLE 7-continued

| Prep. Ex. | Column 2 | Column 3 | DATA |
|---|---|---|---|
| 56 | | | LCMS: MH+ = 342 |
| 57 | | | LCMS: MH+ = 376 |
| 58 | | | LCMS: MH+ = 274 |
| 59 | | | LCMS: MH+ = 288 |
| 60 | | | |
| 61 | | | Yield = 75%<br>LCMS: MH+ = 338 |
| 62 | | | Yield = 52%<br>LCMS: MH+ = 368 |

TABLE 7-continued
| Prep. Ex. | Column 2 | Column 3 | DATA |
|---|---|---|---|
| 63 | 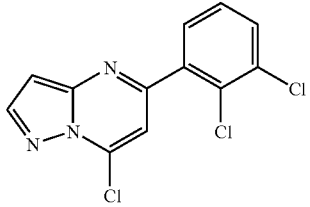 | 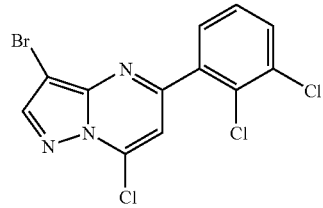 | Yield = 87%<br>LCMS: MH$^+$ = 376 |
| 64 | 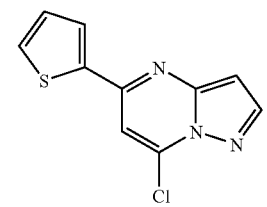 | 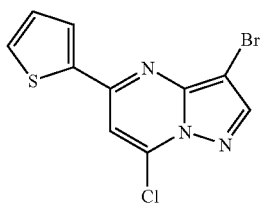 | Yield = 100%<br>LCMS: MH$^+$ = 316 |
| 65 | 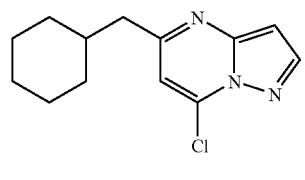 | 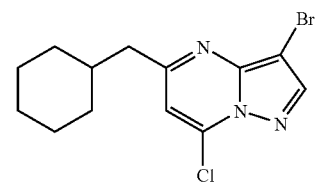 | Yield = 92%<br>LCMS: MH$^+$ = 330 |
| 66 | 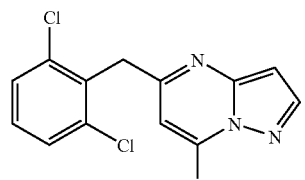 | 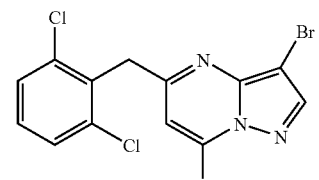 | Yield = 82%<br>LCMS: MH$^+$ = 395 |
| 67 | 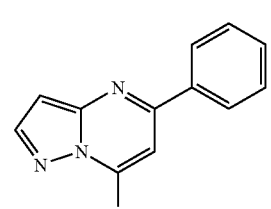 | 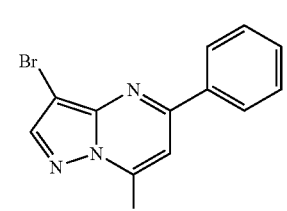 | Yield = 88%<br>LCMS: MH$^+$ = 308 |
| 68 | 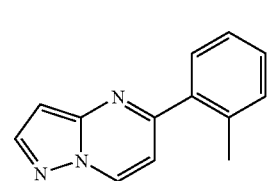 | 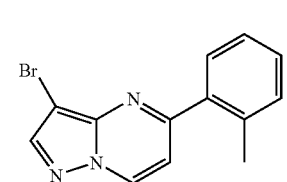 | Yield = 100%<br>LCMS: MH$^+$ = 322 |
| 68.10 | 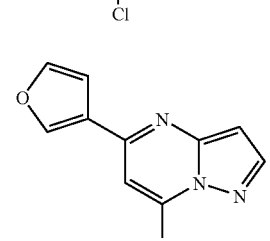 | 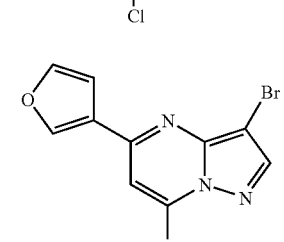 | |

TABLE 7-continued

| Prep. Ex. | Column 2 | Column 3 | DATA |
|---|---|---|---|
| 68.11 | | | |
| 68.12 | | | Yield = 99<br>MH+ = 449 |
| 68.13 | | | Yield = 95<br>MH+ = 449 |
| 68.14 | | | MH+ = 266 |
| 68.15 | | | Yield = quant.<br>MH+ = 314 |

Preparative Example 69

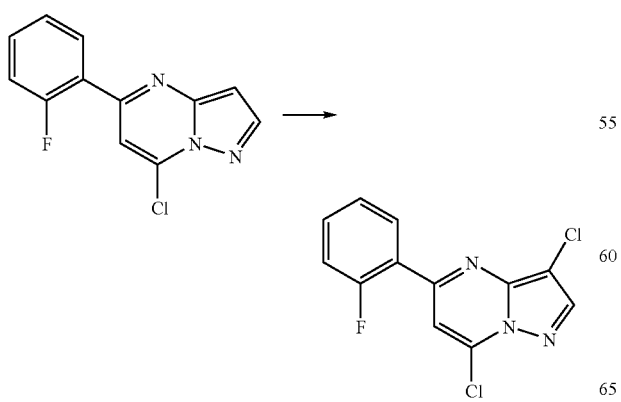

A solution of the compound prepared in Preparative Example 35 (0.3 g, 1.2 mmol) in $CH_3CN$ (15 mL) was treated with NCS (0.18 g, 1.1 eq.) and the resulting solution heated to reflux 4 hours. Additional NCS (0.032 g, 0.2 eq.) added and the resulting solution was stirred at reflux overnight. The reaction mixture was cooled to room temperature, concentrated in vacuo and the residue purified by flash chromatography using a 20% EtOAc in hexanes solution as eluent (0.28 g, 83% yield). LCMS: MH+=282.

Preparative Example 70

By essentially the same procedure set forth in Preparative Example 69 only substituting the compound shown in Column 2 of Table 8, the compound shown in Column 3 of Table 8 was prepared:

TABLE 8

| Prep. Ex. | Column 2 | Column 3 | DATA |
|---|---|---|---|
| 70 | | | Yield = 82%<br>LCMS: MH$^+$ = 286 |

Preparative Example 71

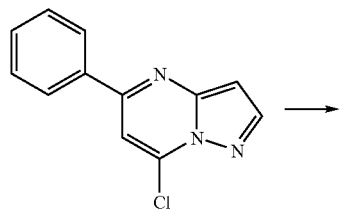

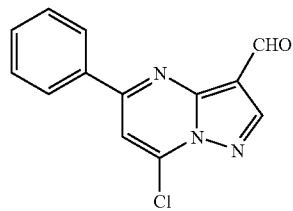

To a solution of the compound from Preparative Example 34 (1.0 g, 4.35 mmol) in DMF (6 mL) was added POCl$_3$ (1.24 mL, 3.05 eq.) and the resulting mixture was stirred at room temperature overnight. The reaction mixture was cooled to 0° C. and the excess POCl$_3$ was quenched by the addition of ice. The resulting solution was neutralized with 1 N NaOH, diluted with H$_2$O, and extracted with CH$_2$Cl$_2$. The combined organics were dried over Na$_2$SO$_4$, filtered and concentrated in vacuo. The crude product was purified by flash chromatography using a 5% MeOH in CH$_2$Cl$_2$ solution as eluent (0.95 g, 85% yield). LCMS: MH$^+$=258.

Preparative Example 72

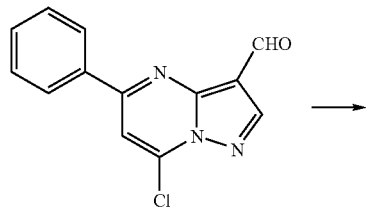

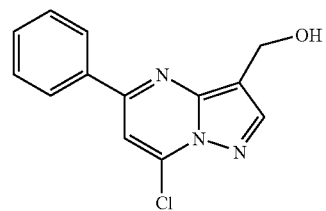

To a solution of the product of Preparative Example 71 (0.25 g, 0.97 mmol) in THF was added NaBH$_4$ (0.041 g, 1.1 eq.) and the resulting solution was stirred at room temperature overnight. The reaction mixture was quenched by the addition of H$_2$O and extracted with CH$_2$Cl$_2$. The combined organics were dried over Na$_2$SO$_4$, filtered, and concentrated under reduced pressure. The crude product was purified by flash chromatography using a 60:40 hexanes:EtOAc mix as eluent (0.17 g, 69% yield). LCMS: MH$^+$=260.

Preparative Example 73

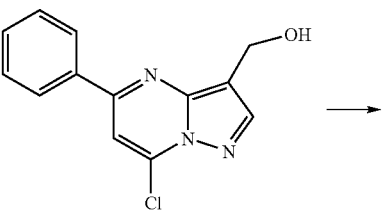

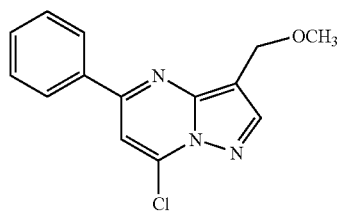

A solution of the compound prepared in Preparative Example 72 (0.12 g, 0.462 mmol), dimethyl sulfate (0.088 mL, 2.0 eq), 50% NaOH (0.26 mL) and catalytic Bu$_4$NBr in CH$_2$Cl$_2$ (4 mL) was stirred at room temperature overnight. The reaction mixture was diluted with H$_2$O and extracted with CH$_2$Cl$_2$. The combined organics were dried over Na$_2$SO$_4$, filtered, and concentrated under reduced pressure.

The crude product was purified by flash chromatography using a 30% EtOAc-in-hexanes solution as eluent (0.062 g, 48% yield).

Preparative Example 74

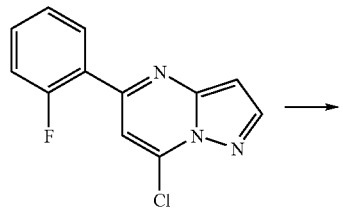

The compound prepared in Preparative Example 35 (0.3 g, 1.2 mmol), K₂CO₃ (0.33 g, 2 eq.), and 4-aminopyridine (1.1 eq.) are reacted in 5 mL CH₃CN for two days and concentrated under reduced pressure. The residue is partitioned between H₂O and CH₂Cl₂. The organic layer is dried over Na₂SO₄, filtered and, concentrated. The crude product is purified by flash chromatography using a 5% (10% NH₄OH in MeOH) solution in CH₂Cl₂ as eluent to give the desired product.

Preparative Example 75

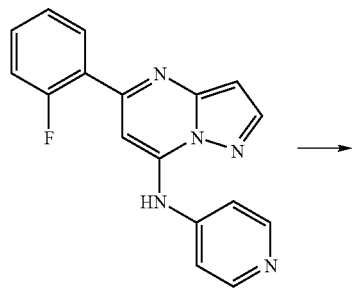

The compound from Preparative Example 74 (0.91 mmol), BOC₂O (0.22 g, 1.1 eq), and DMAP (0.13 g, 1.1 eq.) are reacted in dioxane (10 mL) at room temperature for 3 days. Additional BOC₂O (0.10 g, 0.5 eq.) is added and stirred for 4 hours. It is then concentrated in vacuo, diluted with saturated NaHCO₃ (15 mL), and extracted with CH₂Cl₂ (2×100 mL). The combined organic layers are dried over Na₂SO₄, filter, and concentrate under reduced pressure. The crude product is purified by flash chromatography using a 5% (10% NH₄OH in MeOH) solution in CH₂Cl₂ as eluent to give the product.

Preparative Example 76

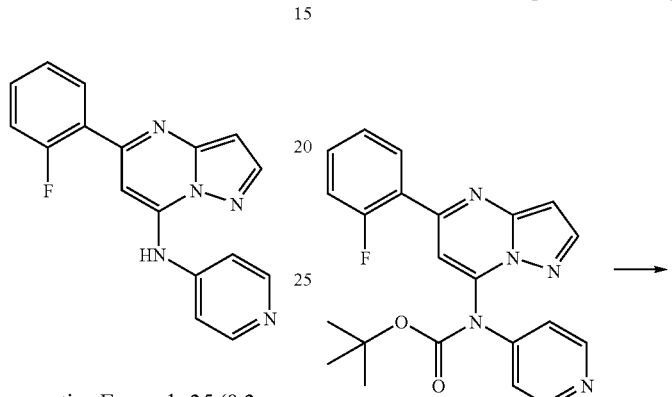

By essentially the same procedure set forth in Preparative Example 54 only substituting the compound prepared in Preparative Example 75, the above product is prepared.

Preparative Example 77

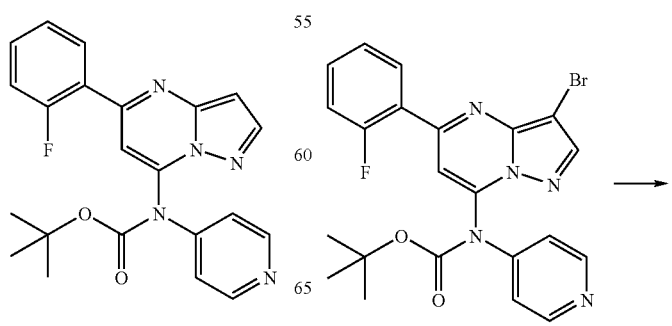

-continued

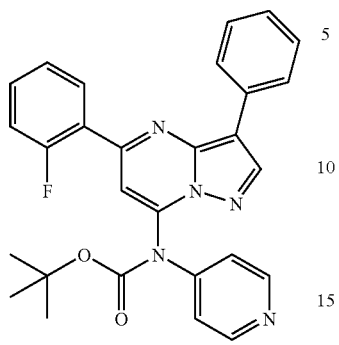

The product of Preparative Example 76 (0.3 mmol), phenylboronic acid (0.073 g, 2.0 eq.), $K_3PO_4$ (0.19 g, 3.0 eq.), and $Pd(PPh_3)_4$ (0.017 g, 5 mol %) are reacted in refluxing DME (16 mL) and $H_2O$ (4 mL) for 7 hours. The resulting solution is cooled to room temperature, diluted with $H_2O$ (10 mL), and extracted with $CH_2Cl_2$ (3×50 mL). The combined organics are dried over $Na_2SO_4$, filtered, and concentrated. The crude product is purified by flash chromatography using a 2.5% (10% $NH_4OH$ in MeOH) in $CH_2Cl_2$ solution as eluent to obtain the product.

Preparative Example 78

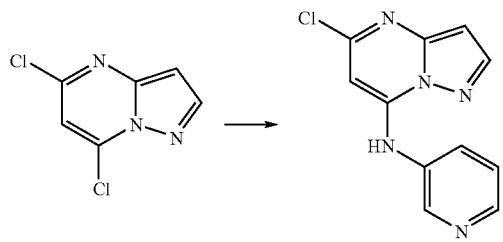

To a solution of the compound prepared in Preparative Example 53.15 (0.25 g, 1.3 mmol) in dioxane (5 mL) is added $iPr_2NEt$ (0.47 mL, 2.0 eq.) and 3-aminomethylpyridine (0.15 ml, 1.1 eq.). The resulting solution is stirred at room temperature 72 hours. The reaction mixture is diluted with $H_2O$ and extracted with EtOAc. The combined organics are washed with $H_2O$ and saturated NaCl, dried over $Na_2SO_4$, filtered, and concentrated in vacuo. The crude product is purified by flash chromatography.

Preparative Examples 79-81

By essentially the same procedure set forth in Preparative Example 78 only substituting the compound shown in Column 2 of Table 8.10, the compounds shown in Column 3 of Table 8.10 are prepared.

TABLE 8.10

| Prep. Ex. | Column 2 | Column 3 |
|---|---|---|
| 79 | ![Cl-pyrazolopyrimidine-Cl] | ![Cl-pyrazolopyrimidine-NH-4-pyridyl] |
| 80 | ![Cl-pyrazolopyrimidine-Br-Cl] | ![Cl-pyrazolopyrimidine-Br-NH-3-pyridyl] |
| 81 | ![Cl-pyrazolopyrimidine-Br-Cl] | ![Cl-pyrazolopyrimidine-Br-NH-4-pyridyl] |

Preparative Example 82

![Cl-pyrazolopyrimidine-Br with NH-3-pyridyl → Boc protected product]

By essentially the same procedure set forth in Preparative Example 75 only substituting the compound from Preparative Example 80, the above compound is prepared.

Example 1

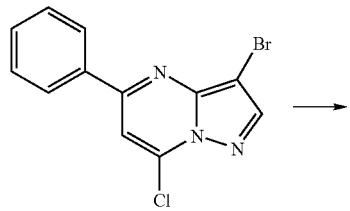

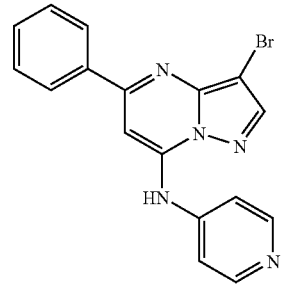

-continued

The product from Preparative Example 54 (0.875 mmol), 4-aminopyridine (0.12 g, 1.3 eq.), and K₂CO₃ (0.24 g, 2 eq.) are reacted in CH₃CN (5 mL) as described in Preparative Example 74 to obtain the product.

Examples 2-46.18

By following essentially the same procedure described in Example 1 only using the reactants shown in Columns 2 and 3 of Table 9, the products shown in Column 4 can be obtained.

TABLE 9

| Ex. | Column 2 | Column 3 | Column 4 |
|-----|----------|----------|----------|
| 2 | | | |
| 3 | | | |
| 4 | | | |

TABLE 9-continued

| Ex. | Column 2 | Column 3 | Column 4 |
|---|---|---|---|
| 5 | 5-(2-fluorophenyl)-3,7-dichloropyrazolo[1,5-a]pyrimidine | 3-aminopyridine | 5-(2-fluorophenyl)-3-chloro-7-(pyridin-3-ylamino)pyrazolo[1,5-a]pyrimidine |
| 6 | 5-(2-fluorophenyl)-3,7-dichloropyrazolo[1,5-a]pyrimidine | 4-aminopyridine | 5-(2-fluorophenyl)-3-chloro-7-(pyridin-4-ylamino)pyrazolo[1,5-a]pyrimidine |
| 7 | 5-(2-chlorophenyl)-3-bromo-7-chloropyrazolo[1,5-a]pyrimidine | 4-aminopyridine | 5-(2-chlorophenyl)-3-bromo-7-(pyridin-4-ylamino)pyrazolo[1,5-a]pyrimidine |
| 8 | 5-(2-chlorophenyl)-3-bromo-7-chloropyrazolo[1,5-a]pyrimidine | 3-aminopyridine | 5-(2-chlorophenyl)-3-bromo-7-(pyridin-3-ylamino)pyrazolo[1,5-a]pyrimidine |
| 9 | 5-(3-trifluoromethylphenyl)-3-bromo-7-chloropyrazolo[1,5-a]pyrimidine | 3-aminopyridine | 5-(3-trifluoromethylphenyl)-3-bromo-7-(pyridin-3-ylamino)pyrazolo[1,5-a]pyrimidine |

TABLE 9-continued

| Ex. | Column 2 | Column 3 | Column 4 |
| --- | --- | --- | --- |
| 10 | | | |
| 11 | | | |
| 12 | | | |
| 13 | | | |
| 14 | | | |

TABLE 9-continued

| Ex. | Column 2 | Column 3 | Column 4 |
| --- | --- | --- | --- |
| 15 | | | |
| 16 | | | |
| 17 | | | |
| 18 | | | |
| 19 | | | |

TABLE 9-continued
| Ex. | Column 2 | Column 3 | Column 4 |
| --- | --- | --- | --- |
| 20 | 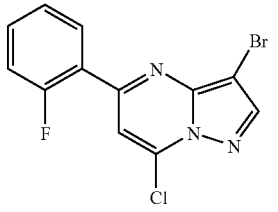 | 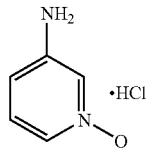 | 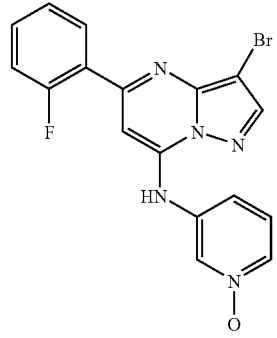 |
| 21 | 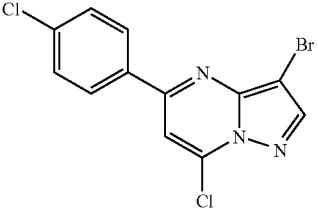 | 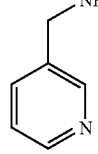 | 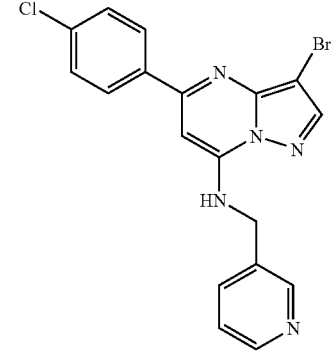 |
| 22 | 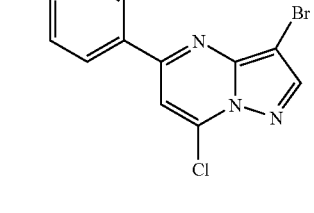 | 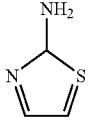 | 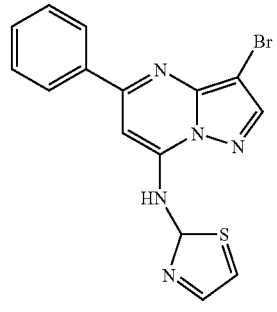 |
| 23 | 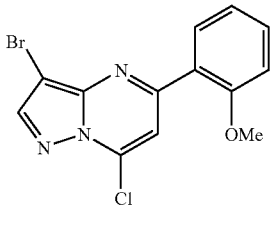 | 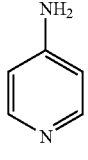 | 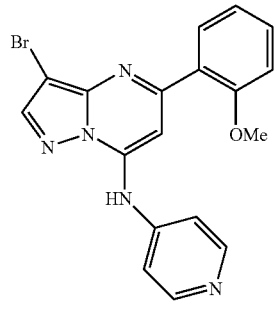 |

TABLE 9-continued

| Ex. | Column 2 | Column 3 | Column 4 |
|---|---|---|---|
| 24 | 3-bromo-5-(2-methoxyphenyl)-7-chloropyrazolo[1,5-a]pyrimidine | 3-aminopyridine | 3-bromo-5-(2-methoxyphenyl)-N-(pyridin-3-yl)pyrazolo[1,5-a]pyrimidin-7-amine |
| 25 | 3-bromo-5-(3,4-dimethoxyphenyl)-7-chloropyrazolo[1,5-a]pyrimidine | 4-aminopyridine | 3-bromo-5-(3,4-dimethoxyphenyl)-N-(pyridin-4-yl)pyrazolo[1,5-a]pyrimidin-7-amine |
| 26 | 3-bromo-5-(3,4-dimethoxyphenyl)-7-chloropyrazolo[1,5-a]pyrimidine | 3-aminopyridine | 3-bromo-5-(3,4-dimethoxyphenyl)-N-(pyridin-3-yl)pyrazolo[1,5-a]pyrimidin-7-amine |
| 27 | 3-bromo-5-(2,3-dichlorophenyl)-7-chloropyrazolo[1,5-a]pyrimidine | 4-aminopyridine | 3-bromo-5-(2,3-dichlorophenyl)-N-(pyridin-4-yl)pyrazolo[1,5-a]pyrimidin-7-amine |
| 28 | 3-bromo-5-(2,3-dichlorophenyl)-7-chloropyrazolo[1,5-a]pyrimidine | 3-aminopyridine | 3-bromo-5-(2,3-dichlorophenyl)-N-(pyridin-3-yl)pyrazolo[1,5-a]pyrimidin-7-amine |

TABLE 9-continued

| Ex. | Column 2 | Column 3 | Column 4 |
|---|---|---|---|
| 29 | | | |
| 30 | | | |
| 31 | | | |
| 32 | | | |
| 33 | | | |

TABLE 9-continued

| Ex. | Column 2 | Column 3 | Column 4 |
|---|---|---|---|
| 34 | | | |
| 35 | | | |
| 36 | | | |
| 37 | | | |
| 38 | | | |

TABLE 9-continued

| Ex. | Column 2 | Column 3 | Column 4 |
| --- | --- | --- | --- |
| 39 | | | |
| 40 | | | |
| 41 | | | |
| 42 | | | |
| 43 | | | |

TABLE 9-continued

| Ex. | Column 2 | Column 3 | Column 4 |
|---|---|---|---|
| 44 | | | |
| 45 | | | |
| 46 | | | |
| 46.10 | | | |
| 46.11 | | | |

TABLE 9-continued

| Ex. | Column 2 | Column 3 | Column 4 |
|---|---|---|---|
| 46.12 | | | |
| 46.13 | | | |
| 46.14 | | | |
| 46.15 | | | |
| 46.16 | | | |

TABLE 9-continued

| Ex. | Column 2 | Column 3 | Column 4 |
|---|---|---|---|
| 46.17 | | | |
| 46.18 | | | |

Example 47

TFA (0.5 mL) was added to a solution of the compound prepared in Preparative Example 76 (0.16 mmol) in CH₂Cl₂ (2.0 mL) at 0° C. and the solution stirred for 2.5 hours. It was stored at 4° C. overnight at which time an additional TFA (0.5 mL) is added. It was stirred for 4 hours and concentrated in vacuo. It was neutralized with 1 N NaOH and extracted with CH₂Cl₂. The combined organic layers were dried over Na₂SO₄, filter, and concentrated under reduced pressure. The crude product was purified by flash chromatography using a 2.5% (10% NH₄OH in MeOH) in CH₂Cl₂ solution as eluent to give the product.

Example 48

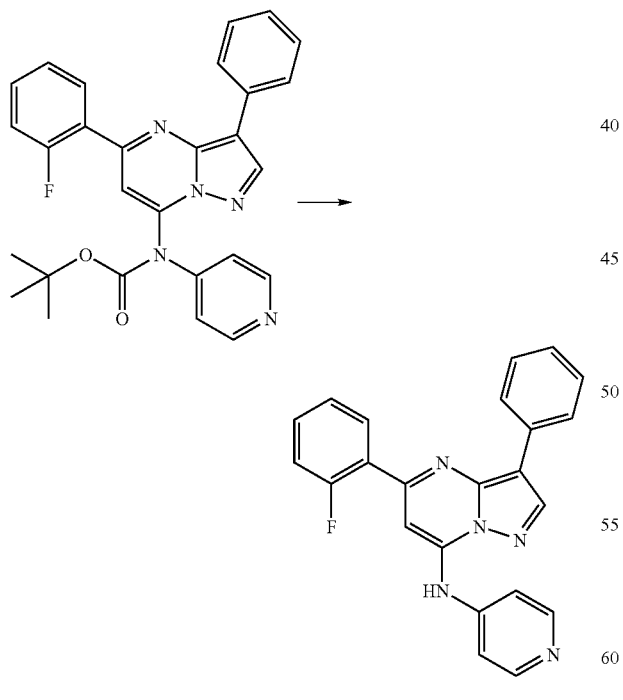

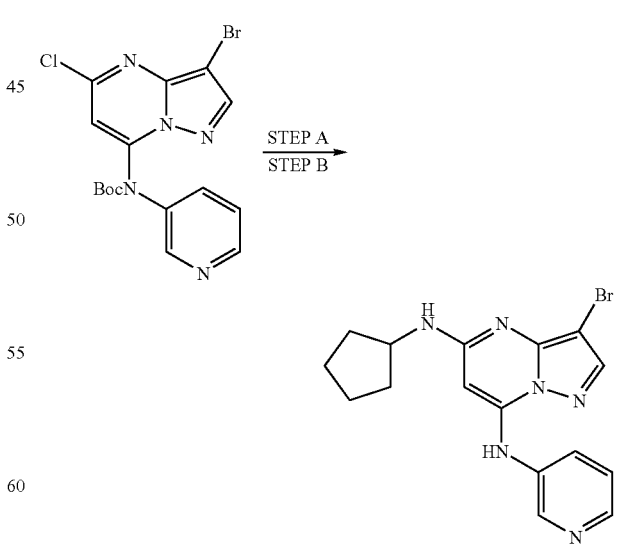

Step A:

To a solution of 5-chloro adduct in dioxane/DIPEA (2.5/1.0) at rt is added cyclopentylamine (1.2 eq.) dropwise. The resulting solution is stirred at reflux for 16 h, cooled to rt, and concentrated under reduced pressure. The crude material is purified by preparative thin-layer chromatography (8×1000 μM).

Step B:

To a solution of the compound prepared in Example 48, Step A in CH$_2$Cl$_2$ at rt is added TFA (5 eq.) dropwise. The resulting solution is stirred for 18 h at rt and is concentrated under reduced pressure. The crude material is redissolved in CH$_2$Cl$_2$ and the organic layer is sequentially washed with sat. aq. NaHCO$_3$ (2×2 mL) and brine (1×2 mL). The organic layer is dried (Na$_2$SO$_4$), filtered, and concentrated under reduced pressure. The crude material is purified by preparative thin-layer chromatography (8×1000 μM).

Examples 49-58

By essentially the same procedure set forth in Example 48 only substituting the chlorides in Column 2 of Table 10 the compounds shown in Column 3 of Table 10 are prepared.

TABLE 10

| Ex. | Column 2 | Column 4 |
|---|---|---|
| 49 | | |
| 50 | | |
| 51 | | |

TABLE 10-continued

| Ex. | Column 2 | Column 4 |
|---|---|---|
| 52 | | |
| 53 | | |
| 54 | | |
| 55 | | |

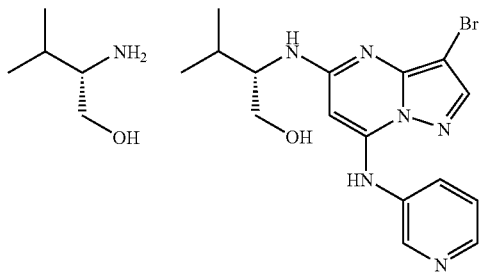
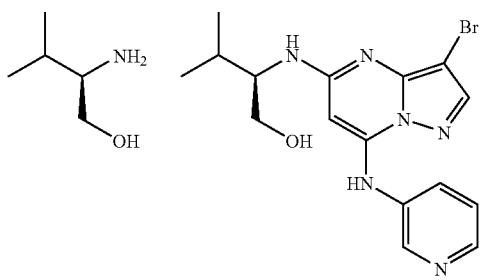
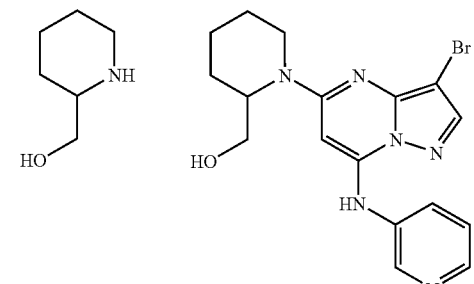
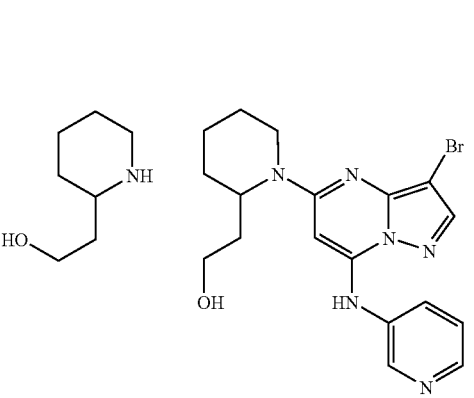

TABLE 10-continued

| Ex. | Column 2 | Column 4 |
|---|---|---|
| 56 | | |
| 57 | | |
| 58 | | |

Example 59

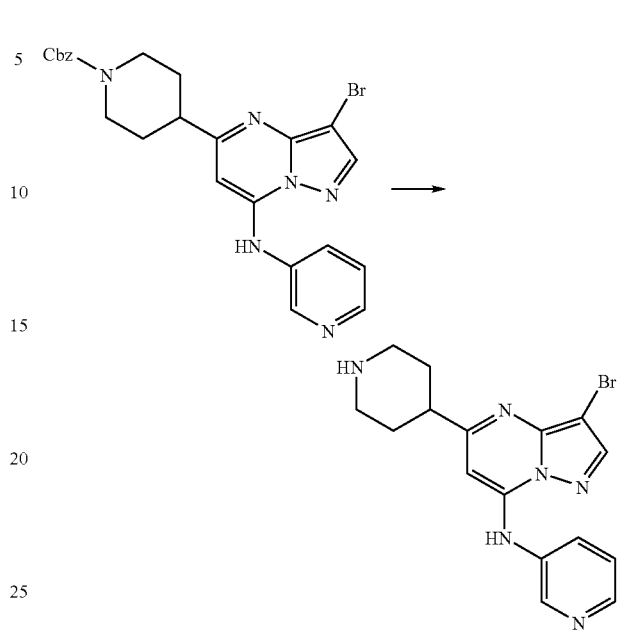

To a solution of the compound prepared in Example 46.14 in anhydrous acetonitrile is added TMSI (4 eq.), dropwise at ambient temperature. After 10 minutes the acetonitrile is removed in vacuo. The resulting yellow foam is treated with 2 N HCl solution (7 mL) and then washed immediately with Et$_2$O (5×). The pH of the aqueous is adjusted to 10 with 50% NaOH (aq) and the product is isolated by saturation of the solution with NaCl (s) followed by extraction with CH$_2$Cl$_2$ (5×) to give the desired product.

Examples 60-62

By essentially the same procedure set forth in Example 58 only substituting the compounds shown in Column 2 of Table 11, the compounds shown in Column 3 of Table 11 were prepared.

TABLE 11

| Ex. | Column 2 | Column 3 |
|---|---|---|
| 60 | | |

TABLE 11-continued

| Ex. | Column 2 | Column 3 |
|---|---|---|
| 61 | (Cbz-piperidinyl pyrazolopyrimidine with Br and 3-pyridylamino) | (piperidinyl pyrazolopyrimidine with Br and 3-pyridylamino) |
| 62 | (Cbz-piperidinyl pyrazolopyrimidine with Br and 4-pyridylamino) | (piperidinyl pyrazolopyrimidine with Br and 4-pyridylamino) |

ASSAY: The assay on the compounds of the present invention may be performed as follows.

BACULOVIRUS CONSTRUCTIONS: Cyclin E is cloned into pVL1393 (Pharmingen, La Jolla, Calif.) by PCR, with the addition of 5 histidine residues at the amino-terminal end to allow purification on nickel resin. The expressed protein is approximately 45 kDa. CDK2 is cloned into pVL1393 by PCR, with the addition of a haemaglutinin epitope tag at the carboxy-terminal end (YDVPDYAS). The expressed protein is approximately 34 kDa in size.

ENZYME PRODUCTION: Recombinant baculoviruses expressing cyclin E and CDK2 are co-infected into SF9 cells at an equal multiplicity of infection (MOI=5), for 48 hrs. Cells are harvested by centrifugation at 1000 RPM for 10 minutes, then pellets lysed on ice for 30 minutes in five times the pellet volume of lysis buffer containing 50 mM Tris pH 8.0, 150 mM NaCl, 1% NP40, 1 mM DTT and protease inhibitors (Roche Diagnostics GmbH, Mannheim, Germany). Lysates are spun down at 15000 RPM for 10 minutes and the supernatant retained. 5 ml of nickel beads (for one liter of SF9 cells) are washed three times in lysis buffer (Qiagen GmbH, Germany). Imidazole is added to the baculovirus supernatant to a final concentration of 20 mM, then incubated with the nickel beads for 45 minutes at 4° C. Proteins are eluted with lysis buffer containing 250 mM imidazole. Eluate is dialyzed overnight in 2 liters of kinase buffer containing 50 mM Tris pH 8.0, 1 mM DTT, 10 mM MgCl2, 100 uM sodium orthovanadate and 20% glycerol. Enzyme is stored in aliquots at −70° C.

IN VITRO KINASE ASSAY: Cyclin E/CDK2 kinase assays are performed in low protein binding 96-well plates (Corning Inc, Corning, N.Y.). Enzyme is diluted to a final concentration of 50 μg/ml in kinase buffer containing 50 mM Tris pH 8.0, 10 mM $MgCl_2$, 1 mM DTT, and 0.1 mM sodium orthovanadate. The substrate used in these reactions is a biotinylated peptide derived from Histone H1 (from Amersham, UK). The substrate is thawed on ice and diluted to 2 μM in kinase buffer. Compounds are diluted in 10% DMSO to desirable concentrations. For each kinase reaction, 20 μl of the 50 μg/ml enzyme solution (1 μg of enzyme) and 20 μl of the 2 μM substrate solution are mixed, then combined with 10 μl of diluted compound in each well for testing. The kinase reaction is started by addition of 50 μl of 2 μM ATP and 0.1 μCi of 33P-ATP (from Amersham, UK). The reaction is allowed to run for 1 hour at room temperature. The reaction is stopped by adding 200 μl of stop buffer containing 0.1% Triton X-100, 1 mM ATP, 5 mM EDTA, and 5 mg/ml streptavidine coated SPA beads (from Amersham, UK) for 15 minutes. The SPA beads are then captured onto a 96-well GF/B filter plate (Packard/Perkin Elmer Life Sciences) using a Filtermate universal harvester (Packard/Perkin Elmer Life Sciences.). Non-specific signals are eliminated by washing the beads twice with 2M NaCl then twice with 2 M NaCl with 1% phosphoric acid. The radioactive signal is then measured using a Top-Count 96 well liquid scintillation counter (from Packard/Perkin Elmer Life Sciences).

$IC_{50}$ DETERMINATION: Dose-response curves are be plotted from inhibition data generated, each in duplicate, from 8 point serial dilutions of inhibitory compounds. Concentration of compound is plotted against % kinase activity, calculated by CPM of treated samples divided by CPM of untreated samples. To generate $IC_{50}$ values, the dose-response curves are then fitted to a standard sigmoidal curve and $IC_{50}$ values are derived by nonlinear regression analysis.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:

1. A method of treating chronic lymphocytic leukemia (CLL), by inhibiting cyclin dependent kinase in a patient comprising administering a therapeutically effective amount of at least one compound represented by the structural formula:

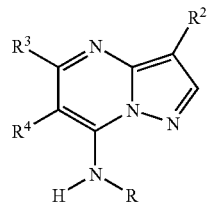

wherein:

R is heteroaryl, wherein said heteroaryl can be unsubstituted or optionally independently substituted with one or more moieties which can be the same or different, each moiety being independently selected from the group consisting of halogen, aryl, cycloalkyl, $CF_3$, $OCF_3$, CN, $-OR^5$, $-NR^5R^6$, $-(CR^4R^5)_nOR^5$, $-C(O)_2R^5$, $-C(O)R^5$, $-C(O)NR^5R^6$, $-SR^6$, $-S(O)_2R^7$, $-S(O)_2NR^5R^6$, $-N(R^5)S(O)_2R^7$, $-N(R^5)C(O)R^7$ and $-N(R^5)C(O)NR^5R^6$;

$R^2$ is selected from the group consisting of $R^9$, alkyl, alkynyl, aryl, heteroaryl, $CF_3$, alkynylalkyl, cycloalkyl, $-C(O)OR^4$, alkyl substituted with 1-6 substitutents independently selected from the group $R^9$,

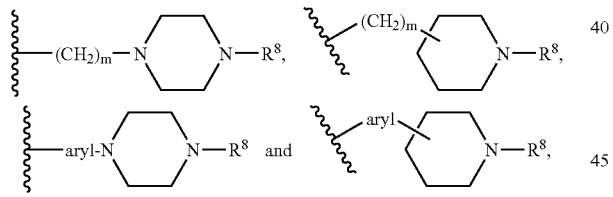

wherein the aryl in the above-noted definitions for $R^2$ can be unsubstituted or optionally substituted with one or more moieties which can be the same or different, each moiety being independently selected from the group consisting of halogen, CN, $-OR^5$, $SR^5$, $-CH_2OR^5$, $-C(O)R^5$, $-SO_3H$, $-S(O)_2R^6$, $-S(O)_2NR^5R^6$, $-NR^5R^6$, $-C(O)NR^5R^6$, $-CF_3$, and $-OCF_3$;

$R^3$ is selected from the group consisting of H, halogen, $-NR^5R^6$, $-C(O)OR^4$, $-C(O)NR^5R^6$, alkyl, alkynyl, cycloalkyl, cycloalkylalkyl, aryl, arylalkyl, heterocyclyl, heteroaryl,

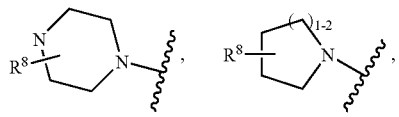

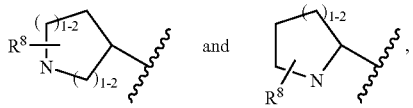

wherein each of said alkyl, cycloalkyl, aryl, arylalkyl, heterocyclyl, heteroaryl for $R^3$ and the heterocyclyl moieties whose structures are shown immediately above for $R^3$ can be substituted or optionally independently substituted with one or more moieties which can be the same or different, each moiety being independently selected from the group consisting of halogen, alkyl, aryl, cycloalkyl, $CF_3$, CN, $-OCF_3$, $-(CR^4R^5)_nOR^5$, $-OR^5$, $-NR^5R^6$, $-(CR^4R^5)_nNR^5R^6$, $-C(O)_2R^5$, $-C(O)R^5$, $-C(O)NR^5R^6$, $-SR^6$, $-S(O)_2R^6$, $-S(O)_2NR^5R^6$, $-N(R^5)S(O)_2R^7$, $-N(R^5)C(O)R^7$ and $-N(R^5)C(O)NR^5R^6$;

$R^4$ is H, halo or alkyl;

$R^5$ is H or alkyl;

$R^6$ is selected from the group consisting of H, alkyl, aryl, arylalkyl, cycloalkyl, heterocyclyl, heteroaryl, and heteroarylalkyl, wherein each of said alkyl, aryl, arylalkyl, cycloalkyl, heterocyclyl, heteroaryl, and heteroarylalkyl can be unsubstituted or optionally substituted with one or more moieties which can be the same or different, each moiety being independently selected from the group consisting of halogen, alkyl, aryl, cycloalkyl, $CF_3$, $OCF_3$, CN, $-OR^5$, $-NR^5R^{10}$, $-N(R^5)$(tertiary Butoxycarbonyl), $-(CR^4R^5)_nOR^5$, $-C(O)_2R^5$, $-C(O)R^5$, $-C(O)NR^5R^{10}$, $-SO_3H$, $-SR^{10}$, $-S(O)_2R^7$, $-S(O)_2NR^5R^{10}$, $-N(R^5)S(O)_2R^7$, $-N(R^5)C(O)R^7$ and $-N(R^5)C(O)NR^5R^{10}$;

$R^{10}$ is selected from the group consisting of H, alkyl, aryl, arylalkyl, cycloalkyl, heterocyclyl, heteroaryl, and heteroarylalkyl, wherein each of said alkyl, aryl, arylalkyl, cycloalkyl, heterocyclyl, heteroaryl, and heteroarylalkyl can be unsubstituted or optionally substituted with one or more moieties which can be the same or different, each moiety being independently selected from the group consisting of halogen, alkyl, aryl, cycloalkyl, $CF_3$, $OCF_3$, CN, $-OR^5$, $-NR^4R^5$, $-N(R^5)$(tertiaryButoxycarbonyl), $-(CR^4R^5)_nOR^5$, $-C(O)_2R^5$, $-C(O)NR^4R^5$, $-C(O)R^5$, $-SO_3H$, $-SR^5$, $-S(O)_2R^7$, $-S(O)_2NR^4R^5$, $-N(R^5)S(O)_2R^7$, $-N(R^5)C(O)R^7$ and $-N(R^5)C(O)NR^4R^5$;

or optionally (i) $R^5$ and $R^{10}$ in the moiety $-NR^5R^{10}$, or (ii) $R^5$ and $R^6$ in the moiety $-NR^5R^6$, may be joined together to form a heterocyclyl moiety, with each of said heterocyclyl moiety being unsubstituted or optionally independently being substituted with one or more $R^9$ groups;

$R^7$ is selected from the group consisting of alkyl, cycloalkyl, aryl, heteroaryl, arylalkyl and heteroarylalkyl, wherein each of said alkyl, cycloalkyl, heteroarylalkyl, aryl, heteroaryl and arylalkyl for $R^7$ can be unsubstituted or optionally independently substituted with one or more moieties which can be the same or different, each moiety being independently selected from the group consisting of halogen, alkyl, aryl, cycloalkyl, $CF_3$, $OCF_3$, CN, $-OR^5$, $-NR^5R^{10}$, $-CH_2OR^5$, $-C(O)_2R^5$, $-C(O)NR^5R^{10}$, $-C(O)R^5$, $-SR^{10}$, $-S(O)_2R^{10}$, $-S(O)_2NR^5R^{10}$, $-N(R^5)S(O)_2R^{10}$, $-N(R^5)C(O)R^{10}$ and $-N(R^5)C(O)NR^5R^{10}$;

$R^8$ is selected from the group consisting of $R^6$, —C(O)NR$^5$R$^{10}$, —CH$_2$OR$^4$, —C(O)OR$^6$, —C(O)R$^7$ and —S(O)$_2$R$^7$;

$R^9$ is selected from the group consisting of halogen, —CN, —NR$^5$R$^6$, —(CH$_2$)$_n$OR$^4$, —C(O)$_2$R$^6$, —C(O)NR$^5$R$^6$, —OR$^6$, —SR$^6$, —S(O)$_2$R$^7$, —S(O)$_2$NR$^5$R$^6$, —N(R$^5$)S(O)$_2$R$^7$, —N(R$^5$)C(O)R$^7$ and —N(R$^5$)C(O)NR$^5$R$^6$;

m is 0 to 4; and n is 1 to 4, or a pharmaceutically acceptable salt thereof, to said patient, wherein said cyclin dependent kinase is CDK1 or CDK2.

2. The method of claim 1, wherein said cyclin dependent kinase is CDK2.

3. The method of claim 1 further comprising administering an amount of at least one second compound, said second compound being selected from the group consisting of cisplatin, doxorubicin, irinotecan, paclitaxel, docetaxel, epothilones, tamoxifen, 5-flourouracil, methoxtrexate, temozolomide, cyclophosphamide, 4-[2-[4-[(11R)-3,10-dibromo-8-chloro-6,11-dihydro-5H-benzo[5,6]cyclohepta[1,2-b]pyridine-11-yl]-1piperidinyl]-2oxoethyl]-1-piperidinecarboxamide, tipifarnib, L778,123 (a farnesyt protein transferase inhibitor), BMS 214662 (a famesyl protein transferase inhibitor), gefitinib, erlotinib hydrochloride, imatinib, interferon alpha-2b (recombinant), ara-C, gemcitabine, uracil mustard, chlormethine, ifosfamide, melphalan, chlorambucil, pipobroman, triethylenemelamine, triethylenethiophoramine, busulfan, carmustine, lomustine, sreptozocin, dacarbazine, floxuridine, 6-mercaptopurine, 6-thiogaunine, fludarabine phosphate, leucovirin, oxaliplatin, pentostatin, vinblastine, vincristine, vindesine, bleomycin, dactinomycin, daunorubicin, epirubicin, idarubicin, mithramycin, mitomycin-C, L-asparaginase, teniposide, 17-alpha-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, vinorelbine, anastrazole, letrozole, capecitabine, raloxifene, or Hexamethylmelamine wherein the amounts of the first compound and said second compound result in a desired therapeutic effect.

4. The method of claim 3, further comprising radiation therapy.

5. A pharmaceutical composition comprising a therapeutically effective amount of at least one compound represented by the structural formula:

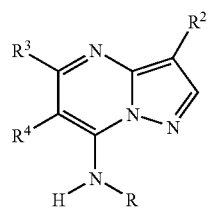

wherein:

R is heteroaryl, wherein said heteroaryl can be unsubstituted or optionally independently substituted with one or more moieties which can be the same or different, each moiety being independently selected from the group consisting of halogen, aryl, cycloalkyl, CF$_3$, OCF$_3$, CN, —OR$^5$, —NR$^5$R$^6$, —C(R$^4$R$^5$)$_n$OR$^5$, —C(O)$_2$R$^5$, —C(O)R$^5$, —C(O)NR$^5$R$^6$, —SR$^6$, —S(O)$_2$R$^7$, —S(O)$_2$NR$^5$R$^6$, —N(R$^5$)S(O)$_2$R$^7$, —N(R$^5$)C(O)R$^7$ and —N(R$^5$)C(O)NR$^5$R$^6$;

$R^2$ is selected from the group consisting of $R^9$, alkyl, alkynyl, aryl, heteroaryl, CF$_3$, alkynylalkyl, cycloalkyl, —C(O)OR$^4$, alkyl substituted with 1-6 substitutents independently selected from the group $R^9$,

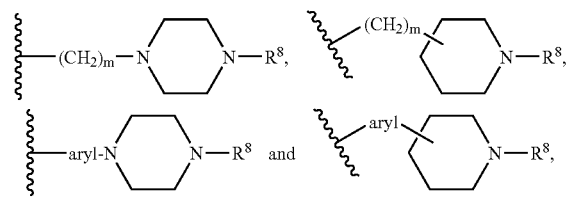

wherein the aryl in the above-noted definitions for $R^2$ can be unsubstituted or optionally substituted with one or more moieties which can be the same or different, each moiety being independently selected from the group consisting of halogen, CN, —OR$^5$, SR$^5$, —CH$_2$OR$^5$, —C(O)R$^5$, —SO$_3$H, —S(O)$_2$R$^6$, —S(O)$_2$NR$^5$R$^6$, —NR$^5$R$^6$, —C(O)NR$^5$R$^6$, —CF$_3$, and —OCF$_3$;

$R^3$ is selected from the group consisting of H, halogen, —NR$^5$R$^6$, —C(O)OR$^4$, —C(O)NR$^5$R$^6$, alkyl, alkynyl, cycloalkyl, cycloalkylalkyl, aryl, arylalkyl, heterocyclyl, heteroaryl,

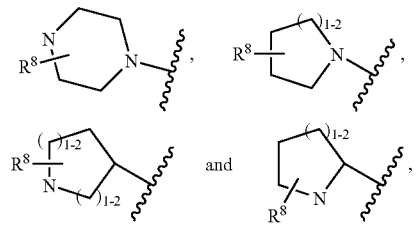

wherein each of said alkyl, cycloalkyl, aryl, arylalkyl, heterocyclyl, heteroaryl for $R^3$ and the heterocyclyl moieties whose structures are shown immediately above for $R^3$ can be substituted or optionally independently substituted with one or more moieties which can be the same or different, each moiety being independently selected from the group consisting of halogen, alkyl, aryl, cycloalkyl, CF$_3$, CN, —OCF$_3$, —(CR$^4$R$^5$)$_n$OR$^5$, —OR$^5$, —NR$^5$R$^6$, —(CR$^4$R$^5$)$_n$NR$^5$R$^6$, —C(O)$_2$R$^5$, —C(O)R$^5$, —C(O)NR$^5$R$^6$, —SR$^6$, —S(O)$_2$R$^6$, —S(O)$_2$NR$^5$R$^6$, —N(R$^5$)S(O)$_2$R$^7$, —N(R$^5$)C(O)R$^7$ and —N(R$^5$)C(O)NR$^5$R$^6$;

$R^4$ is H, halo or alkyl;

$R^5$ is H or alkyl;

$R^6$ is selected from the group consisting of H, alkyl, aryl, arylalkyl, cycloalkyl, heterocyclyl, heteroaryl, and heteroarylalkyl, wherein each of said alkyl, aryl, arylalkyl, cycloalkyl, heterocyclyl, heteroaryl, and heteroarylalkyl can be unsubstituted or optionally substituted with one or more moieties which can be the same or different, each moiety being independently selected from the group consisting of halogen, alkyl, aryl, cycloalkyl, CF$_3$, OCF$_3$, CN, —OR$^5$, —NR$^5$R$^{10}$, —N(R$^5$)(tertiary Butoxycarbonyl), —(CR$^4$R$^5$)$_n$OR$^5$, —C(O)$_2$R$^5$, —C(O)R$^5$, —C(O)NR$^5$R$^{10}$, —SO$_3$H, —SR$^{10}$, —S(O)$_2$R$^7$, —S(O)$_2$NR$^5$R$^{10}$, —N(R$^5$)S(O)$_2$R$^7$, —N(R$^5$)C(O)R$^7$ and —N(R$^5$)C(O)NR$^5$R$^{10}$;

R$^{10}$ is selected from the group consisting of H, alkyl, aryl, arylalkyl, cycloalkyl, heterocyclyl, heteroaryl, and heteroarylalkyl, wherein each of said alkyl, aryl, arylalkyl, cycloalkyl, heterocyclyl, heteroaryl, and heteroarylalkyl can be unsubstituted or optionally substituted with one or more moieties which can be the same or different, each moiety being independently selected from the group consisting of halogen, alkyl, aryl, cycloalkyl, CF$_3$, OCF$_3$, CN, —OR$^5$, —NR$^4$R$^5$, —N(R$^5$)(tertiaryButoxycarbonyl), —(CR$^4$R$^5$)$_n$OR$^5$, —C(O)$_2$R$^5$, —C(O)NR$^4$R$^5$, —C(O)R$^5$, —SO$_3$H, —SR$^5$, —S(O)$_2$R$^7$, —S(O)$_2$NR$^4$R$^5$, —N(R$^5$)S(O)$_2$R$^7$, —N(R$^5$)C(O)R$^7$ and —N(R$^5$)C(O)NR$^4$R$^5$;

or optionally (i) R$^5$ and R$^{10}$ in the moiety —NR$^5$R$^{10}$, or (ii) R$^5$ and R$^6$ in the moiety —NR$^5$R$^6$, may be joined together to form a heterocyclyl moiety, with each of said heterocyclyl moiety being unsubstituted or optionally independently being substituted with one or more R$^9$ groups;

R$^7$ is selected from the group consisting of alkyl, cycloalkyl, aryl, heteroaryl, arylalkyl and heteroarylalkyl, wherein each of said alkyl, cycloalkyl, heteroarylalkyl, aryl, heteroaryl and arylalkyl for R$^7$ can be unsubstituted or optionally independently substituted with one or more moieties which can be the same or different, each moiety being independently selected from the group consisting of halogen, alkyl, aryl, cycloalkyl, CF$_3$, OCF$_3$, CN, —OR$^5$, —NR$^5$R$^{10}$, —CH$_2$OR$^5$, —C(O)$_2$R$^5$, —C(O)NR$^5$R$^{10}$, —C(O)R$^5$, —SR$^{10}$, —S(O)$_2$R$^{10}$, —S(O)$_2$NR$^5$R$^{10}$, —N(R$^5$)S(O)$_2$R$^{10}$, —N(R$^5$)C(O)R$^{10}$ and —N(R$^5$)C(O)NR$^5$R$^{10}$;

R$^8$ is selected from the group consisting of R$^6$, —C(O)NR$^5$R$^{10}$, —CH$_2$OR$^4$, —C(O)OR$^6$, —C(O)R$^7$ and —S(O)$_2$R$^7$;

R$^9$ is selected from the group consisting of halogen, —CN, —NR$^5$R$^6$, —(CH$_2$)$_n$OR$^4$, —C(O)$_2$R$^6$, —C(O)NR$^5$R$^6$, —OR$^6$, —SR$^6$, —S(O)$_2$R$^7$, —S(O)$_2$NR$^5$R$^6$, —N(R$^5$)S(O)$_2$R$^7$, —N(R$^5$)C(O)R$^7$ and —N(R$^5$)C(O)NR$^5$R$^6$;

m is 0 to 4; and n is 1 to 4, or a pharmaceutically acceptable salt thereof in combination with at least one pharmaceutically acceptable carrier.

6. The pharmaceutical composition of claim 5, additionally comprising one or more additional compounds selected from the group consisting of cisplatin, doxorubicin, etoposide, irinotecan, topotecan, paclitaxel, docetaxel, epothilones, tamoxifen, 5-flourouracil, methoxtrexate, temozolomide, cyclophosphamide, 4-[2-[4-[(11R)-3,10-dibromo-8-chloro-6,11-dihydro-5H-benzo[5,6]cyclohepta[1,2-b]pyridine-11-yl]-1-piperidinyl]-2-oxoethyl]-1-piperidinecarboxamide, tipifarnib, L778,123 (a farnesyt protein transferase inhibitor), BMS 214662 ( a famesyl protein transferase inhibitor), gefitinib, erlotinib hydrochloride, imatinib, interferon alpha-2b (recombinant), ara-C, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, 6-mercaptopurine, 6-thiogaunine, fludarabine phosphate, leucovirin, oxaliplatin, pentostatin, vinblastine, vincristine, vindesine, dactinomycin, daunorubicin, epirubicin, idarubicin, mithramycin, mitomycin-C, L-asparaginase, teniposide, 17-alpha-ethinylestradiol, diethylstilbestrol, testosterone, prednisone, flouxymesterone, dromostanolone propionate, testolactone, megestrolacetate, methylprednisolone, methyltestosterone, prednisolone, triamcinolone, chlorotrianisene, hydoroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, vinorelbine, anastrazole, letrazole, capecitabine, raloxifene, or Hexamethylmelamine.

7. the pharmaceutical composition of claim 6 wherein said additional compound is temozolomide.

8. The pharmaceutical composition of claim 5, wherein the pharmaceutical composition is administered together, concurrently or sequentially, with temozolommide.

9. The pharmaceutical composition of claim 5, wherein said pharmaceutical composition is administered together, concurrently or sequentially, with radiation therapy.

10. The pharmaceutical composition of claim 6, wherein at least one of the additional compounds are administered together, concurrently or sequentially, with radiation therapy.

11. A method of treating chronic lymphocytic leukemia (CLL), comprising administering the pharmaceutical composition of claim 5 to a patient in need thereof.

12. A method of treating chronic lymphocytic leukemia (CLL), comprising administering the pharmaceutical composition of claim 6 to a patient in need thereof chronic lymphocytic leukemia (CLL).

* * * * *

UNITED STATES PATENT AND TRADEMARK OFFICE
CERTIFICATE OF CORRECTION

PATENT NO. : 7,470,695 B2
APPLICATION NO. : 11/395974
DATED : December 30, 2008
INVENTOR(S) : Guzi et al.

Page 1 of 1

It is certified that error appears in the above-identified patent and that said Letters Patent is hereby corrected as shown below:

In the Claims:

Claim 3, col. 97, line 17, please correct "doxorubicin, irinotecan, paclitaxel," to:
-- doxorubicin, etoposide, irinotecan, topotecan, paclitaxel, --

Claim 3, col. 97, line 21, please correct "1piperidinyl]-2oxoethyl]" to:
-- 1-piperidinyl]-2-oxoethyl] --

Claim 6, col. 100, line 16, please correct "vindesine, dactinomycin" to:
-- vindesine, bleomycin, dactinomycin --

Claim 12, col. 100, lines 44 & 45, please delete the words "chronic lymphocytic leukemia (CLL)" making the sentence end with the word "thereof"

Signed and Sealed this

Twentieth Day of October, 2009

David J. Kappos
*Director of the United States Patent and Trademark Office*